United States Patent
Eddaoudi et al.

(10) Patent No.: US 9,139,599 B1
(45) Date of Patent: Sep. 22, 2015

(54) 2-PERIODIC METAL-ORGANIC FRAMEWORKS (MOFS) AS SUPERMOLECULAR BUILDING LAYERS (SBLS) FOR MAKING TARGETED 3-PERIODIC MOFS

(71) Applicants: Mohamed Eddaoudi, Tampa, FL (US); Jarrod F. Eubank, Land O' Lakes, FL (US)

(72) Inventors: Mohamed Eddaoudi, Tampa, FL (US); Jarrod F. Eubank, Land O' Lakes, FL (US)

(73) Assignees: University of South Florida, Tampa, FL (US); King Abdullah University of Science and Technology, Thuwal (SA)

( * ) Notice: Subject to any disclaimer, the term of this patent is extended or adjusted under 35 U.S.C. 154(b) by 63 days.

(21) Appl. No.: 13/911,505

(22) Filed: Jun. 6, 2013

Related U.S. Application Data

(60) Provisional application No. 61/656,055, filed on Jun. 6, 2012.

(51) Int. Cl.
  *C07F 1/08* (2006.01)
  *C07F 19/00* (2006.01)

(52) U.S. Cl.
  CPC .................................. *C07F 1/08* (2013.01)

(58) Field of Classification Search
  USPC ................................ 546/2; 548/101; 556/115
  See application file for complete search history.

(56) References Cited

U.S. PATENT DOCUMENTS 8,034,952 B2 * 10/2011 Eddaoudi et al. ............. 548/103
8,900,352 B2 * 12/2014 Wilmer et al. ................. 96/108

OTHER PUBLICATIONS

Nouar, F. et al. : Supermolecular building blocks (SBBs) for the design and synthesis of highly porous metal-organic frameworks. J. Am. Chem. Soc., vol. 130, pp. 1833-1835, 2008.*

Zhang, S. et al.: New three dimensional porous metal organic framework with tetrazole functionalized aromatic carboxylic acid: synthesis, structure, and gas adsorption proprties. lnorg. Chem., vol. 49, pp. 11581-11586, 2010.*

Eubank, J. et al.: The next chapter in MOF pillaring strategies: Trigonal heterofunctional ligands to access targeted high-connected three dimensional nets, isoreticular platforms. J. Am. Chem. Soc., vol. 133, pp. 17532-17535, 2011.*

Li, Y., Liu, L., Subramani, R., Pan, Y., Liu, B., Yang, Y., . . . & Dong, M. (2011). Building layer-by-layer 3D supramolecular nanostructures at the terephthalic acid/stearic acid interface. Chemical Communications, 47(32), 9155-9157.

Choi, E. Y., Barron, P. M., Novotny, R. W., Son, H. T., Hu, C., & Choe, W. (2008). Pillared Porphyrin Homologous Series: Intergrowth in Metal—Organic Frameworks. Inorganic Chemistry, 48(2), 426-428.

Yu, L. Q., Huang, R. D., Chi, Y. N., & Hu, C. W. (2008). Preparation, Structure and Properties of 3D Supramolecular Architecture, on the Basis of Hydrogen Bonds and π-π Stacking Between 2D Layers, with Windmill Building Blocks. Chemical Research in Chinese Universities, 24(3), 251-254.

* cited by examiner

*Primary Examiner* — Charanjit Aulakh
(74) *Attorney, Agent, or Firm* — Thomas Horstemeyer, LLP

(57) ABSTRACT

Embodiments of the present disclosure provide for chemical assemblies, multidimensional metal-organic frameworks (MOFs), supermolecular building layers (SBLs), inorganic molecular building blocks (MBBs), organic MBBs (designed ligands), methods of making each, and methods of using each, and the like. In an embodiment, the composition can be used in catalysis, separations, gas storage, and drug delivery.

14 Claims, 12 Drawing Sheets

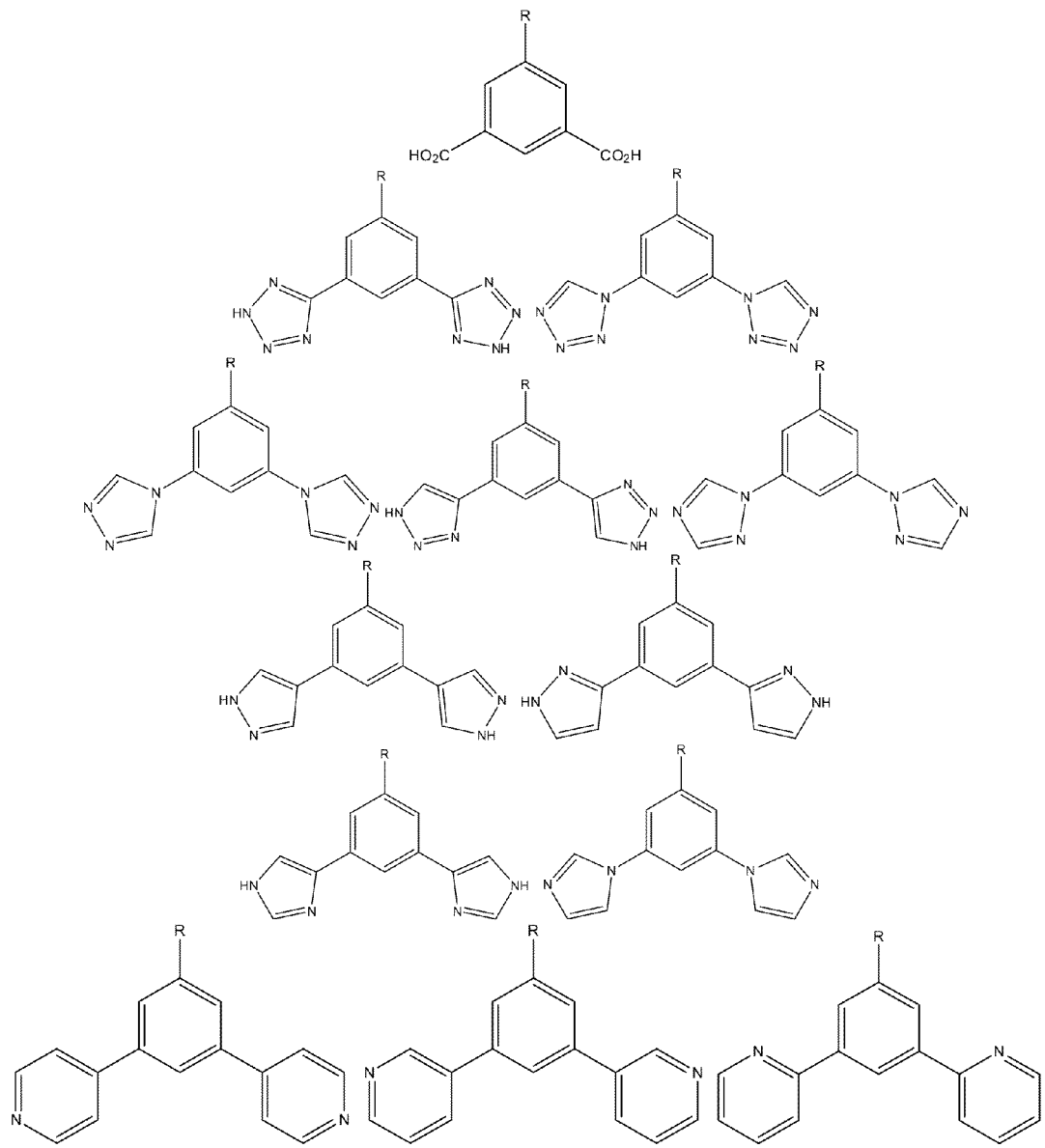
FIG. 1.1A

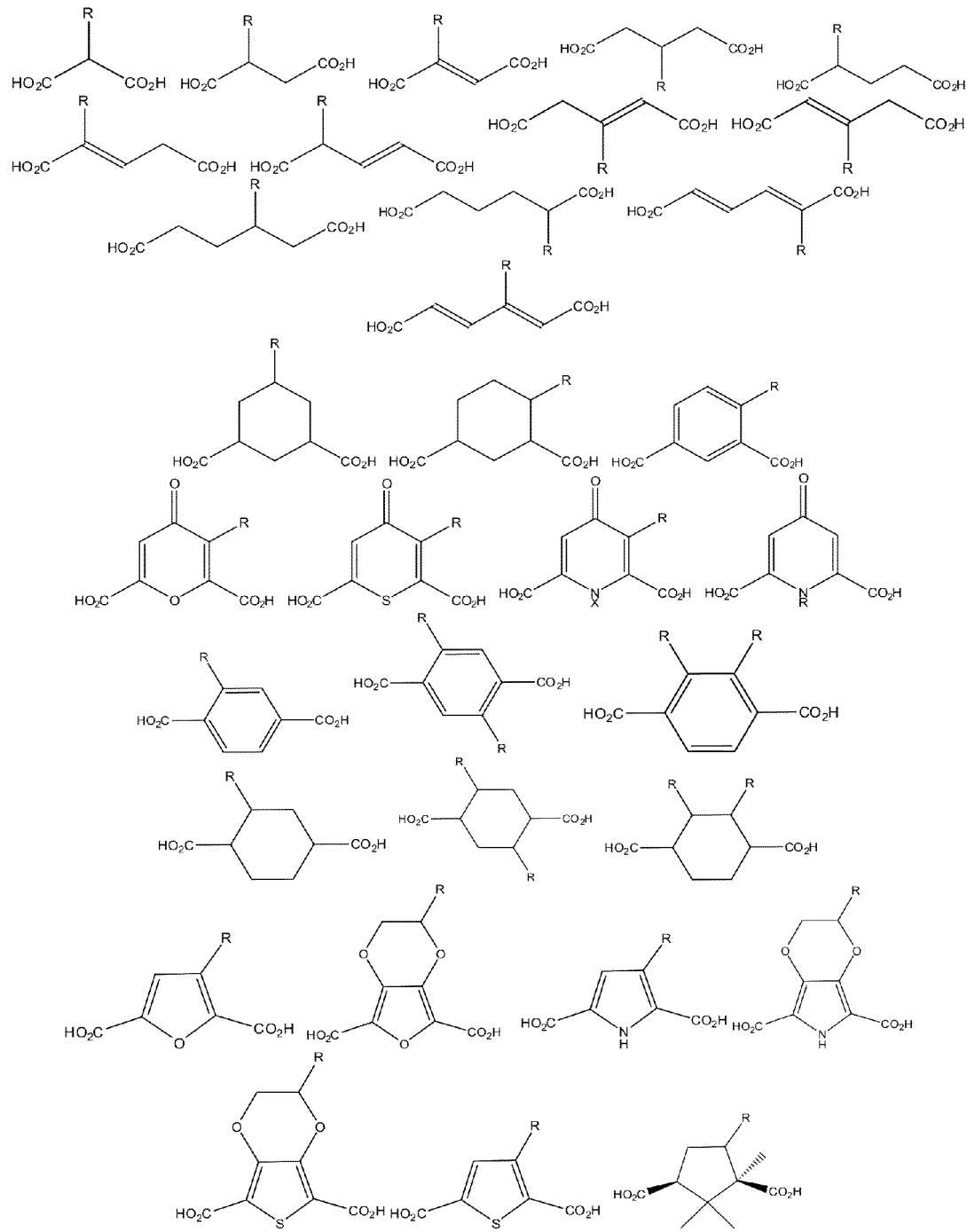
FIG. 1.1B

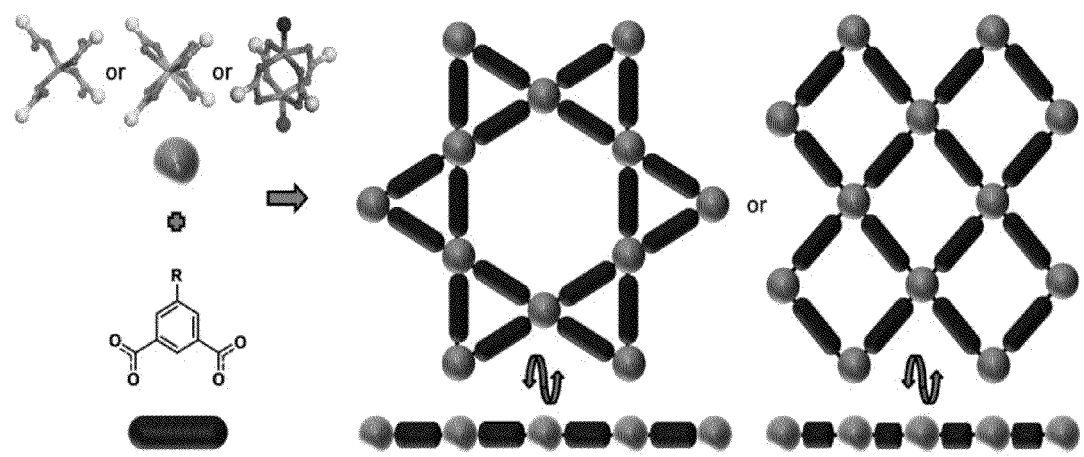
FIG. 2.1A
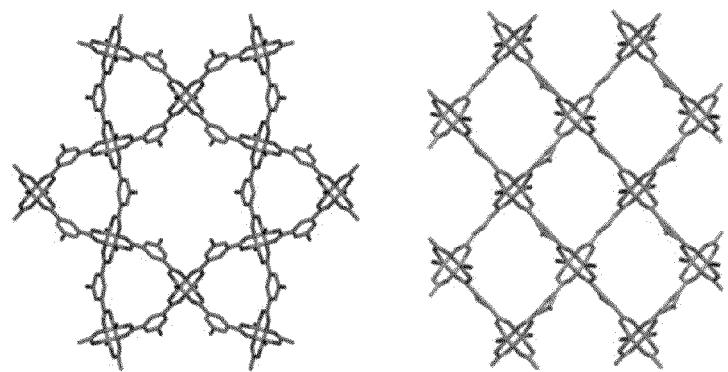
FIG. 2.1B

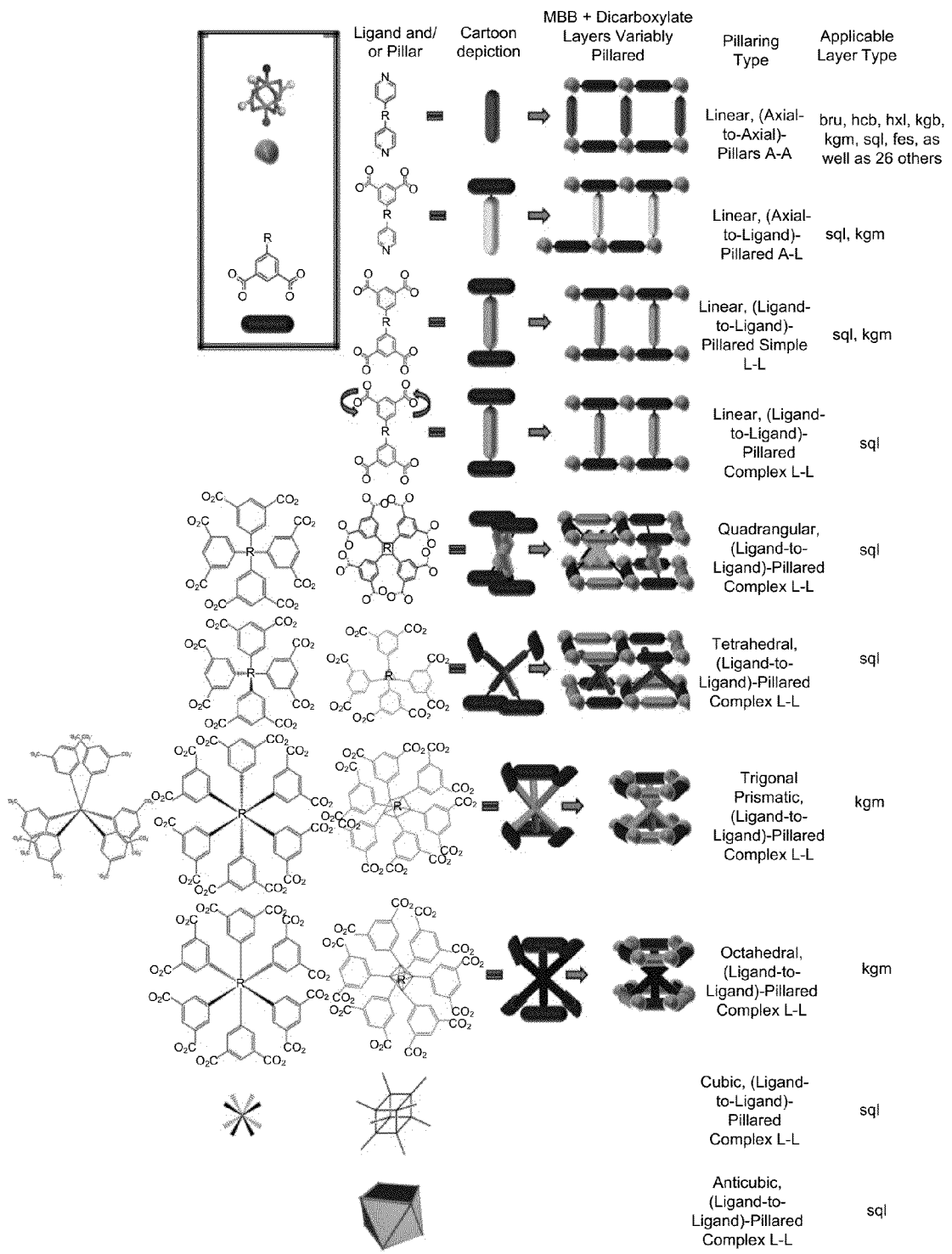
FIG. 2.1C

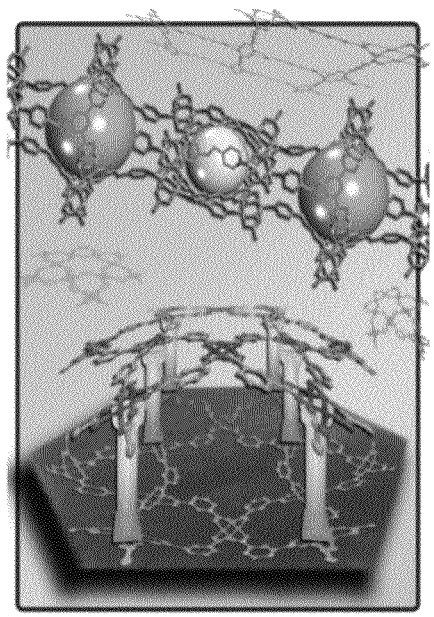
FIG. 2.1D
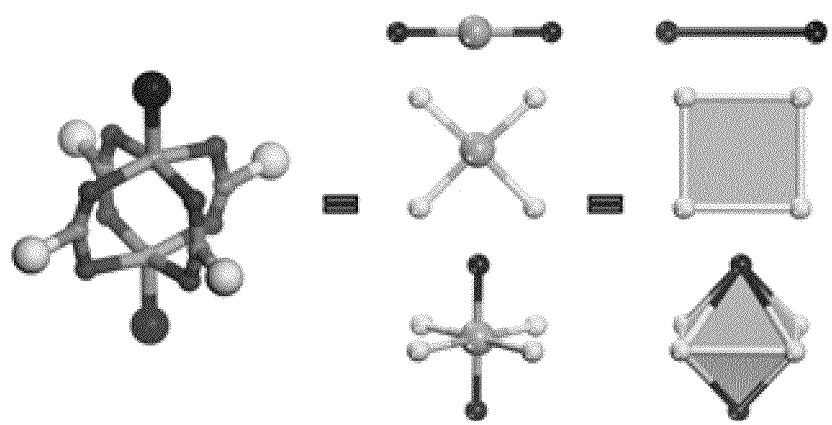
FIG. 3.1

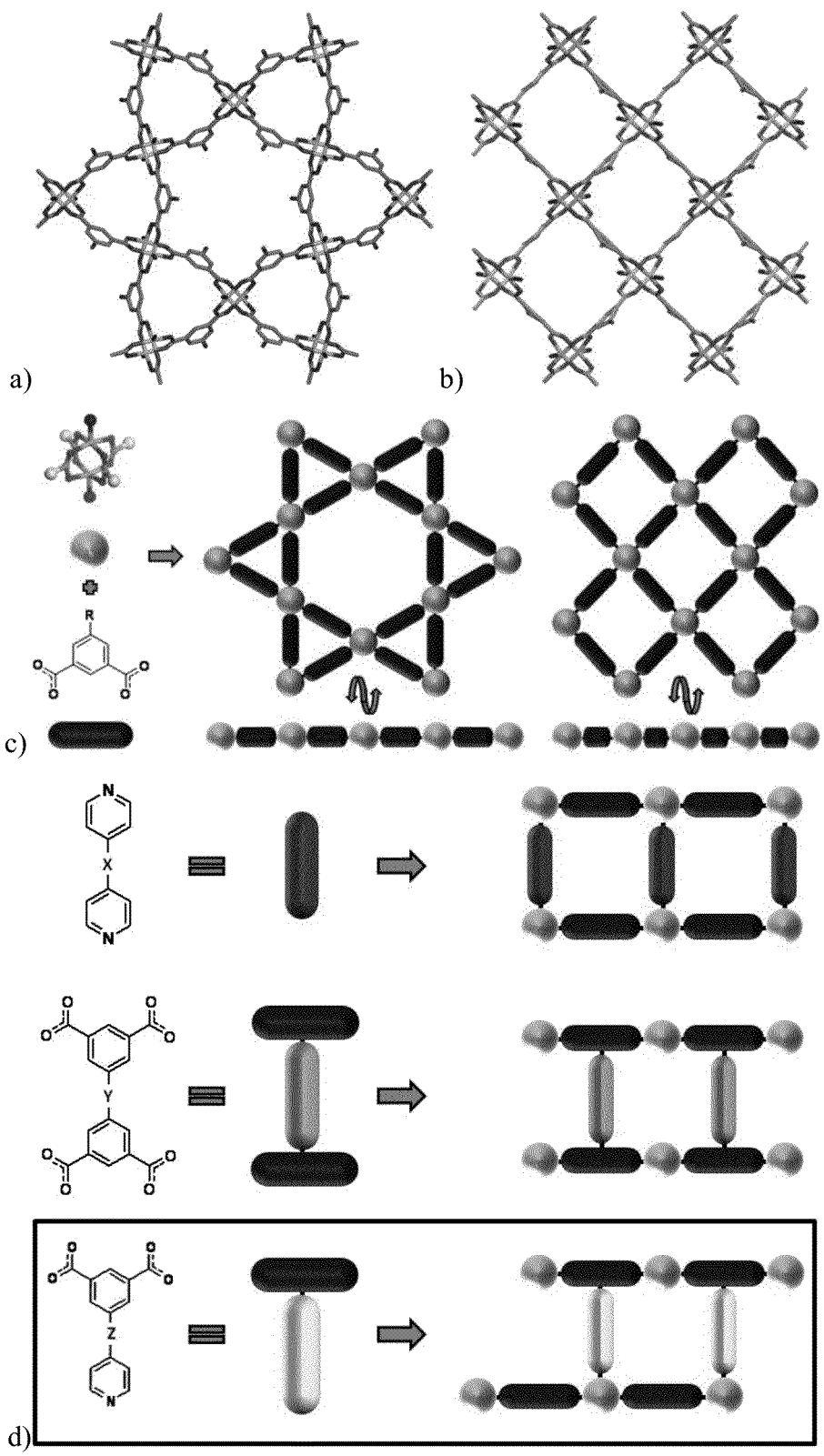
FIG. 3.2

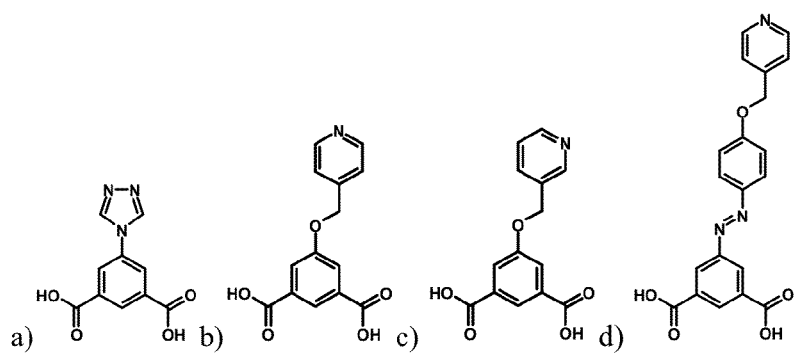
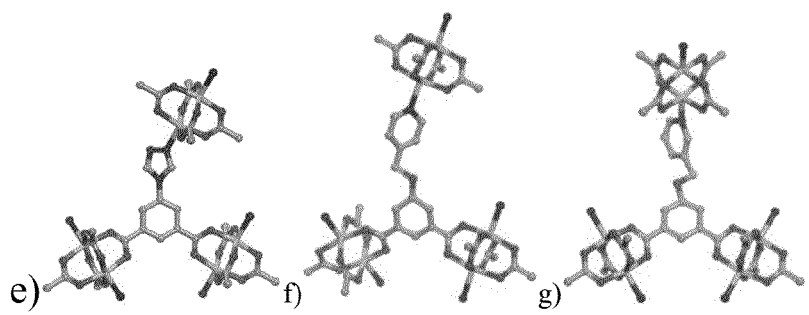
FIG. 3.3
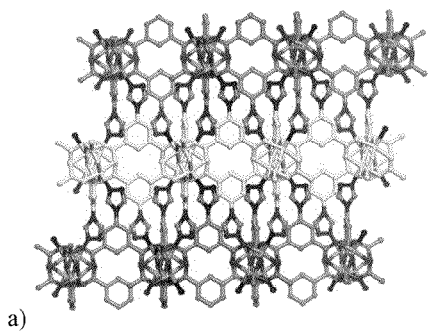
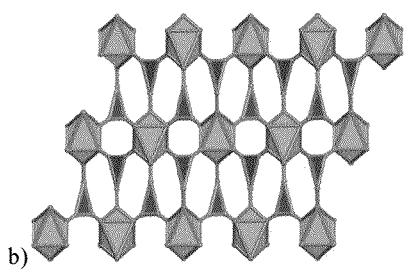
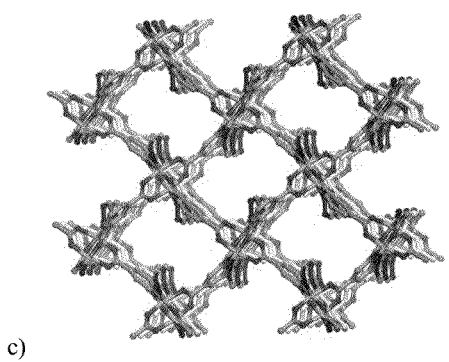
FIG. 3.4

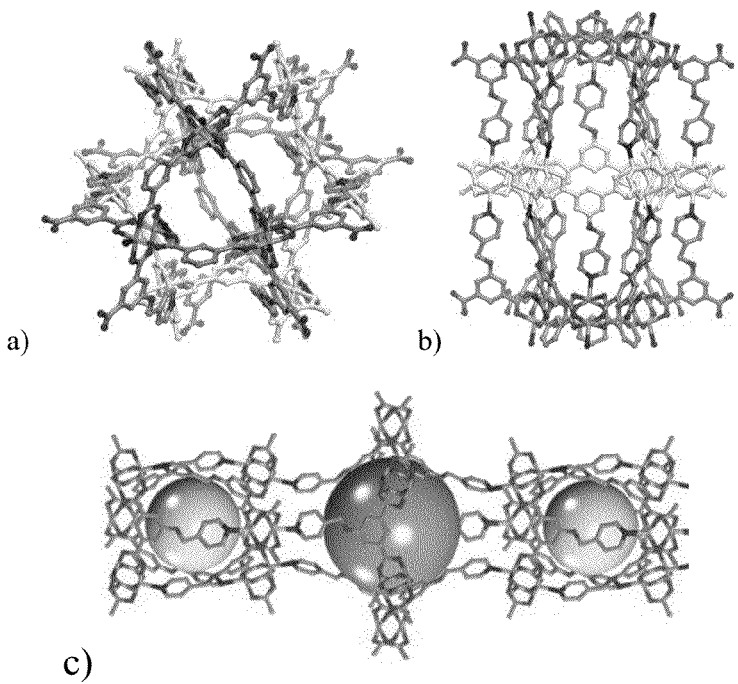
FIG. 3.5
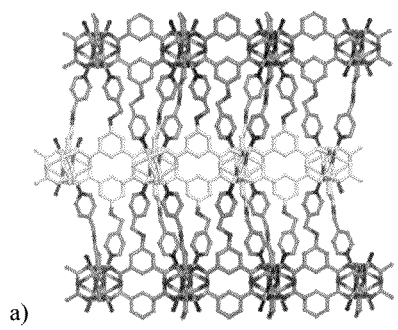
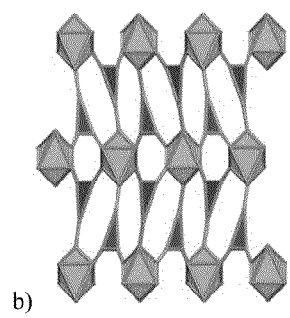
FIG. 3.6
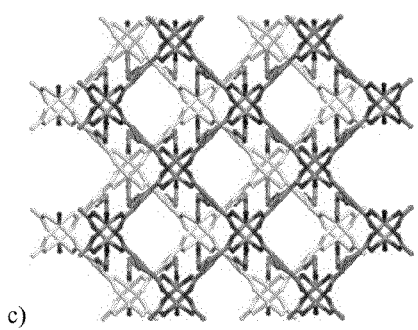

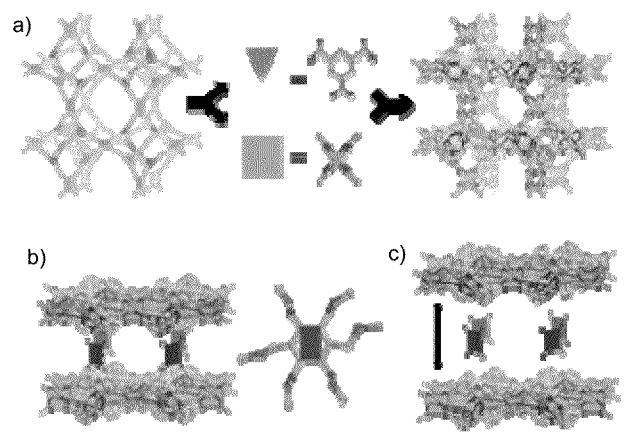
FIG. 4.1
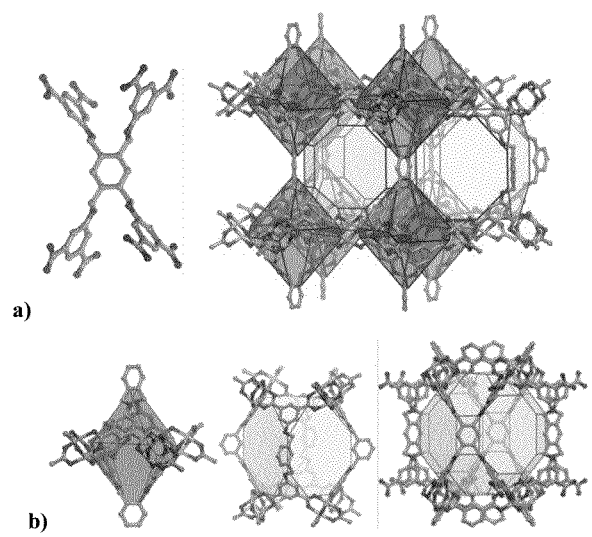
FIG. 4.2

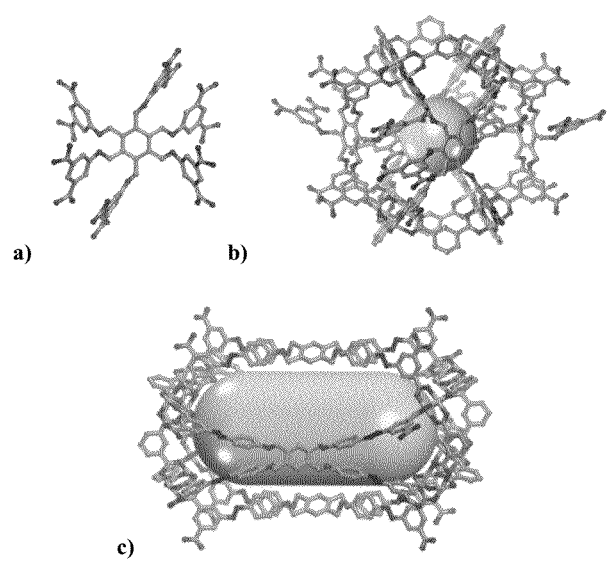
FIG. 4.3

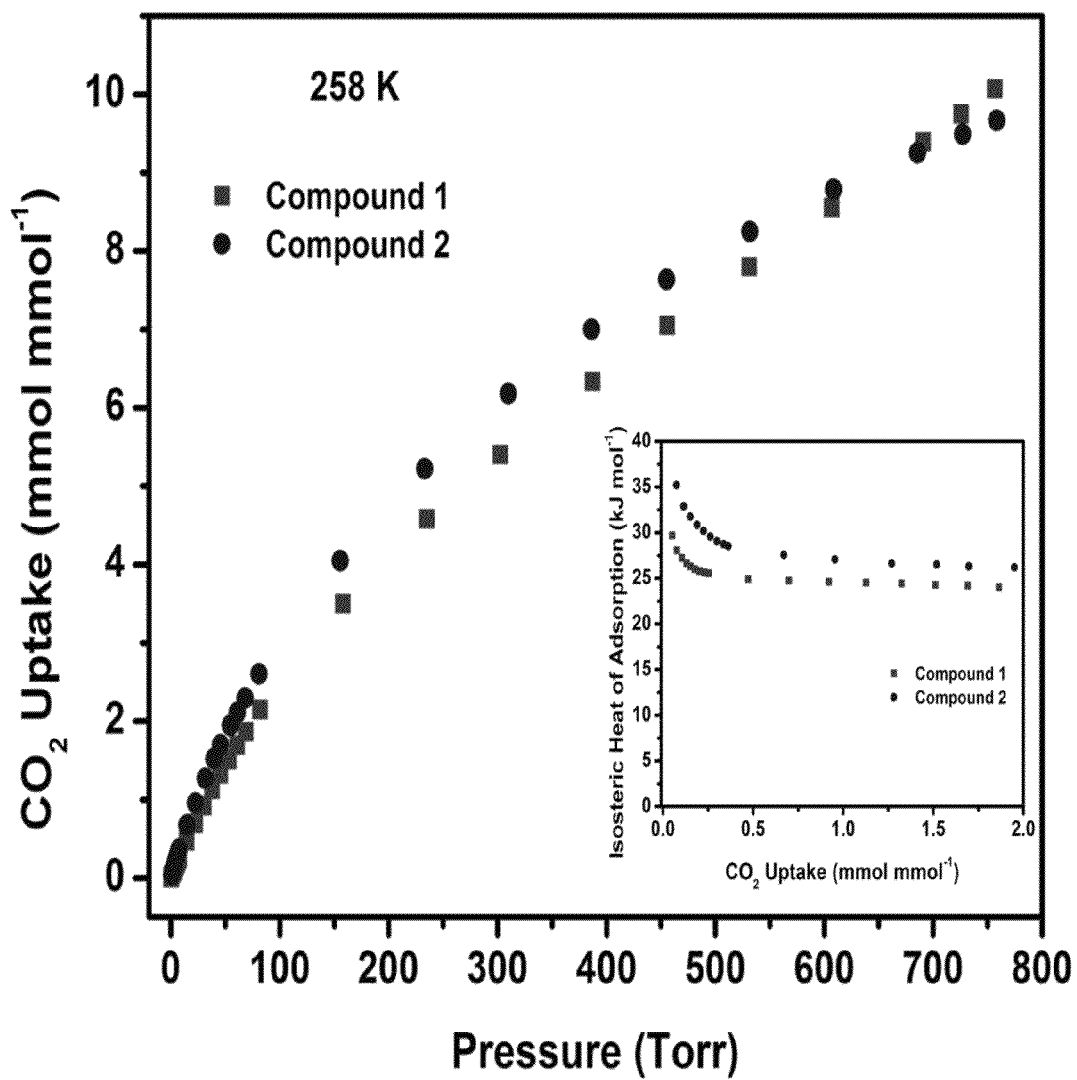
FIG. 4.4a

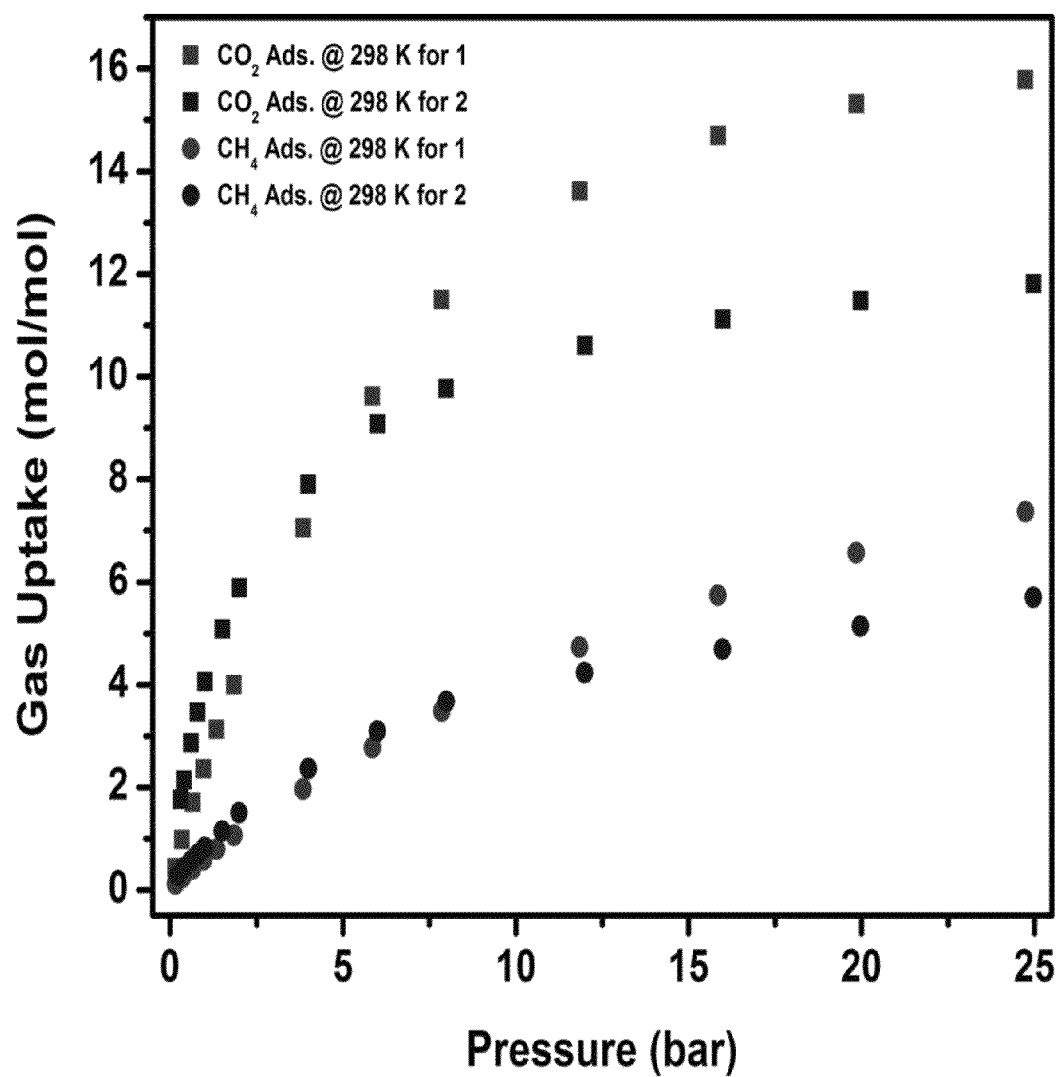
FIG. 4.4b

US 9,139,599 B1

2-PERIODIC METAL-ORGANIC FRAMEWORKS (MOFS) AS SUPERMOLECULAR BUILDING LAYERS (SBLS) FOR MAKING TARGETED 3-PERIODIC MOFS

CROSS-REFERENCE TO RELATED APPLICATION

This application claims priority to U.S. provisional application entitled "2-PERIODIC METAL-ORGANIC FRAMEWORKS (MOFS) AS SUPERMOLECULAR BUILDING LAYERS (SBLS) FOR MAKING TARGETED 3-PERIODIC MOFS," having Ser. No. 61/656,055, filed on Jun. 6, 2012, which is entirely incorporated herein by reference.

FEDERAL SPONSORSHIP

This invention was made with Government support under Contract/Grant No. DMR 0548117, awarded by the National Science Foundation. The Government has certain rights in this invention.

BACKGROUND

Metal-organic frameworks (MOFs) is an emerging class of porous solid-state materials with significant contributions in numerous application areas including, but not limited to, catalysis, separations, gas storage, and drug delivery. In this typical class of periodic solids, there has been great progress toward design, due largely to the ability to target specific [molecular] building blocks with given geometry and directionality (e.g. squares, tetrahedra, etc.) prior to the assembly process.

Recently, there has been an increased effort to generate 3D porous MOFs via "pillaring" these layered MOFs. One approach, referred to here as axial-to-axial (A-A) pillaring, takes additional advantage of the auxiliary axial metal sites of a paddlewheel configuration, which are typically occupied by terminal ligands like water or pyridine. In this case, pairs of terminal ligands are replaced by a ditopic (bridging) ligand, that can coordinate the axial positions of two dimer units from neighboring layers resulting in bridged MOF layers based on six-connected dimer units.

Another pillaring method involves what we call ligand-to-ligand (L-L) pillaring, where specific ligands are selected to simultaneously contain two bridging ligand moieties that pillar adjacent layers through the covalent linkage of the tetracarboxylate ligand. When the 4-connected ligand coordinates to form the 4-connected paddlewheel MBB, the resulting 3D MOF is based on a (4,4)-connected topology (e.g., nbo-MOFs).

However, alternative pillaring strategies are needed to form other types of layered MOFs.

SUMMARY

Embodiments of the present disclosure provide for chemical assemblies, multidimensional metal-organic frameworks (MOFs), supermolecular building layers (SBLs), inorganic molecular building blocks (MBBs), organic MBBs (designed ligands), methods of making each, methods of using each, and the like.

An exemplary embodiment of the present disclosure includes a chemical assembly, having: a multidimensional metal-organic framework (MOF) having a plurality of supermolecular building layers (SBLs), wherein the SBL includes an inorganic molecular building block (MBB) and one or more of a bridging ligand, a pillar, or a hybrid of the bridging ligand and the pillar, wherein one or more of the bridging ligand the pillar, or the hybrid of the bridging ligand and the pillar, includes one or more moieties that is independently selected from the group consisting of: a polycarboxylic acid moiety, a polytetrazole moiety, a polytriazole moiety, a polypyrazole moiety, and a polypyridyl moiety.

An exemplary embodiment of the present disclosure includes a chemical assembly, having: a supermolecular building layer (SBL), wherein the SBL includes an inorganic molecular building block (MBB) and one or more of a bridging ligand, a pillar, or a hybrid of the bridging ligand and the pillar, wherein one or more of the bridging ligand, the pillar, or the hybrid of the bridging ligand and the pillar, includes one or more moieties that is independently selected from the group consisting of: a polycarboxylic acid moiety, a polytetrazole moiety, a polytriazole moiety, a polypyrazole moiety, and a polypyridyl moiety.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1A illustrates one suitable (i.e., bridging) polycarboxylic acid for SBL formation (when combined with the applicable inorganic MBB (detailed below)) versus analogous polytetrazoles, polytriazoles, polypyrazoles, polyimidazoles, and polypyridyls, respectively.

FIG. 1.1B illustrates some other suitable dicarboxylic acids for forming SBLs.

FIG. 2.1A illustrates a representative 2-periodic kgm and sql layers, respectively, form in situ coordination of the building units at the left (i.e., MOF formation).

FIG. 2.1B illustrates representative 2-periodic kgm-MOF and sql-MOF, respectively, based on 5-R-isophthalate bridging ligand and the latter paddlewheel MBB FIG. 2.1C illustrates representative ligand/pillar strategies that can be used to form various complexes having different layer types.

FIG. 2.1D illustrates a rendering showing the concept of "pillaring" the 2D MOF layers (SBLs).

FIG. 3.1 illustrates a $M_2(O_2CR)_4A_2MBB$ that can function as a linear linker, square MBB, or octahedral MBB.

FIG. 3.2$a$) illustrates a layer segment of a kgm-MOF made from 5-NR,-1,3-BDC and $M_2(O_2CR)_4A_2MBB$. FIG. 3.2$b$) illustrates a layer segment of a sql-MOF made from 5-NR$_n$-1,3-BDC and $M_2(O_2CR)_4A_2MBB$. FIG. 3.2$c$) illustrates a scheme showing the derivation of corresponding nets, Kagome lattice and square lattice, respectively (overhead and side views). FIG. 3.2$d$) illustrates a scheme representing the various layered MOF (side view) pillaring techniques using exemplary ligands; axial-to-axial (dark gray, linear), ligand-to-ligand (black-gray-black, "I"-shaped) and ligand-to-axial (black-light gray, "T"-shaped).

FIGS. 3.3$a$-$d$) illustrate bifunctional trigonal ligands used in this study; $H_2L1$, $H_2L2$, $H_2L3$, and $H_2L4$, of lengths ~8.4, ~11.3, ~11.3, and ~18 Å, respectively. FIGS. 3.3$e$-$g$) illustrate an example of the coordination mode of the L1, L2, and L3 ligands, respectively, when coordinated to the $M_2(O_2CR)_4A_2$, MBB.

FIGS. 3.4$a$-$c$) illustrate crystal structures. FIG. 3.4$a$) illustrates structure 1 having pillared square grid layers. FIG. 3.4$b$) illustrates polyhedral representations (dark gray triangles and gray octahedra) of this net shows the layers of octahedra (square lattice) pillared by triangles (ligand). FIG. 3.4c) illustrates that the layers stack in a staggered fashion. C=gray, O=dark gray, N=black, Cu=light gray; H atoms omitted and one layer shown monochrome for clarity.

FIGS. 3.5a-b) illustrate the crystal structure of 2 showing pillared Kagomé layers (one layer in monchrome), resulting in the structure shown in FIG. 3.5c) that has hourglass-shaped channels with two primary types of cavities (represented as light gray and gray spheres). C=gray, O=dark gray, N=black, Cu=light gray; H atoms are omitted for clarity.

FIG. 3.6a) illustrates crystal structures of 4 which have pillared square grid layers. FIG. 3.6b) illustrates the polyhedral representations (dark gray triangles and gray octahedra) of this net shows the layers of octahedra (square lattice) pillared by triangles (ligand). FIG. 3.6c) illustrates that the layers stack in a staggered fashion. C=gray, O=dark gray, N=black, Cu=light gray; H atoms are omitted and one layer is shown in monochrome for clarity.

FIG. 4.1a) illustrates the substitution of the vertex figures in the augmented tbo network, tbo-a, with analogous chemical entities results in a tbo-MOF. FIG. 4.1b) illustrates tbo-MOFs can be targeted from sql (gray rod layer) SBLs linked by 4-connected core pillars (dark gray squares), which can be functionalized. FIG. 4.1c) illustrates the extension of the ligand between core (dark gray) and BDC results in greater distance between SBLs and increased confined space.

FIG. 4.2a) illustrates structure L1: a tetra-isophthalate ligand connected through alkoxy links to a 4-connected benzene core and representative section from the crystal structure of 1, showing polyhedral cages. FIG. 4.2b) illustrates each type of polyhedral cage in 1; truncated tetrahedron (dark gray), truncated cube (light gray), and truncated cuboctahedron (gray).

FIG. 4.3a) illustrates L2: a functionalized version of L1. FIG. 4.3b) illustrates a representation of the largest cage from the 3D tbo-MOF, 2, open space reduced due to pendant groups. FIG. 4.3c) illustrates a representation of one nanocapsule cage from the 3D tbo-MOF, 3. The vdw sphere/cylinder is shown in gray.

FIG. 4.4a) illustrates $CO_2$ sorption isotherms for 1 and 2 at 258 K and $Q_{st}$ for $CO_2$ in 1 and 2 (insert). FIG. 4.4b) illustrates $CO_2$ and $CH_4$ high pressure sorption isotherms for 1 and 2 collected at 298 K.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic chemistry, organometallic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

The term "substituted" refers to any one or more hydrogens on the designated atom that can be replaced with a selection from the indicated group, provided that the designated atom's normal valence is not exceeded (though charged and radical variants are acceptable (e.g., $RNH_3^+$ versus $RNH_2$), and that the substitution results in a suitably stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic mono-cyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl, and phenanthryl. The bonds can be attached to any of the rings.

General Discussion:

Embodiments of the present disclosure provide for chemcial assemblies, multidimensional metal-organic frameworks (MOFs), supermolecular building layers (SBLs), inorganic molecular building blocks (MBBs), organic MBBs (designed ligands), methods of making each, and methods of using each, and the like. In an embodiment, the composition can be used in catalysis, separations, gas storage, and drug delivery.

Embodiments of the present disclosure provide for metal-organic frameworks (MOFs) having a specific underlying network topology. In an embodiment, the MOFs can be designed and synthesized utilizing pre-targeted supermolecular building layers (SBLs), where the overall framework remains constant while expansion (e.g., selection of ligands and/or pillars) of the confined space (e.g., porosity) is simple and functionalities can readily be introduced to target specific desirable applications (e.g., MOF platforms for $CO_2$ capture, gas separation, controlled drug release, etc.).

In general, an embodiment of the present disclosure includes a multidimensional metal-organic framework (MOF) having a plurality of supermolecular building layers (SBLs). In an embodiment, the SBL includes a bridging ligand (that can be part of a pillar) and an inorganic molecular building block (MBB). In an embodiment, the MOF can be porous and can be three dimensional so that molecules can be disposed (e.g., captured) within the MOF. Embodiments of the MOF, SBL, the inorganic MBB, and organic MBB, are described below and in the Examples.

MOFs from Supermolecular Building Layers (SBLs) Using Designed Ligands:

According to the Reticular Chemistry Structure Resource (RCSR, http://rcsr.anu.edu.au/), there are only 6 layers (i.e., 2-periodic nets) that are edge transitive, which are the most suitable targets in crystal chemistry: brucite (bru), honeycomb (hcb, 6^3), hexagonal lattice (hxl, 3^6), Kagomé dual (kgd), Kagomé lattice (kgm, 3.6.3.6), and square lattice (sql, 4^4). In the RCSR, there are an additional 33 layers that are not edge transitive (i.e., more complex), but might be targetable in crystal chemistry and are included within the scope of the present disclosure. Layered metal-organic frameworks (MOFs) based on many of these underlying nets (e.g., sql-MOFs, hcb-MOFs, and kgm-MOFs) have already been designed and synthesized via the molecular building block (MBB) approach, where specific inorganic and organic moieties are chosen for their specific geometry and directionality.

Embodiments of the present disclosure use MOF layers as building entities, which we refer to as supermolecular building layers (SBLs), in the construction of 3D MOF materials (also referred to as 3-periodic) based on stacking and pillaring of 2D layers (also referred to as 2-periodic). Judicious ligand selection and design is also a factor, as the ligand(s) play(s) the role of inorganic MBB bridge (independent of the pillar), pillar or connector (independent of the bridging ligand) between adjacent layers, or both (a hybrid of bridging ligand and pillar combined). In an embodiment, the topology of the SBL can be any one of the layer topologies, for example, the layer can have a topology selected from: sql, kgm, hcb, bru, hxl, and kgd.

Embodiments of the present disclosure describe several potential systems from this approach. In an embodiment, the ligand can include one or more coordinating N-, S-, or O-donor functional groups. In an embodiment, the bridging ligand can be polycarboxylic acid ligands (e.g., where some can have additional heterofunctionality for pillaring such as an N-donor functional group), where these and the corresponding inorganic clusters can be formed in situ. In an embodiment, the ligand can include one or more of the following coordinating groups; amides (including sulfonamide and phosphoramides), sulfinic acids, sulfonic acids, phosphonic acids, phosphates, phosphodiesters, phosphines, boronic acids, boronic esters, borinic acids, borinic esters, nitrates, nitrites, nitriles, nitro, nitroso, thiocyanates, cyanates, azos, azides, imides, imines, amines, acetals, ketals, ethers, esters, aldehydes, ketones, alcohols, thiols, sulfides, disulfides, sulfoxides, sulfones, sulfinic acids, thiones, and thials. In an embodiment, the bridging ligand can include one or more moieties that is independently selected from the group consisting of: a polycarboxylic acid moiety, a polytetrazole moiety, a polytriazole moiety, a polypyrazole moiety, and a polypyridyl moiety. In an embodiment, the ligand can include polytetrazoles ligands, polytriazoles ligands, polypyrazoles ligands, and polypyridyls ligands. Exemplary embodiments of the ligands can include those described in FIGS. 1.1A and 1.1B and in the ligand design sections below.

FIG. 1.1A illustrates one suitable (i.e., bridging) polycarboxylic acid for SBL formation (when combined with the applicable inorganic MBB (detailed below)) and analogous polytetrazole, polytriazoles, polypyrazoles, polyimidazoles, and polypyridyls, respectively. In an embodiment, R=any length connection to the pillar/core (i.e., the point of extension) (e.g., a hydrocarbon, ether, ester, amide, sulfur containing group, combinations thereof, and the like, having from 1 to 50 atoms or more). R can include, for example, one or more of the following chemical moieties: —H, —OH, —OR, —COOH, —COOR, —CONH$_2$, —NH$_2$, —NHR1, —NR1R2, —SH, —SR, —SO$_2$R1, —SO$_2$H, —SOR1, R1, alkyl, alkenyl, akynyl, phenyl, biphenyl, azo, and halo (including F, Cl, Br, and I), where each occurrence of R1 or R2, independently, may be hydrocarbyl or substituted hydrocarbyl (e.g., derived from: substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted aryl, or substituted or unsubstituted araalkyl)

FIG. 1.1B illustrates other suitable dicarboxylic acids for forming SBLs. In an embodiment, R=any length connection to the pillar/core (i.e., the point of extension) such as those described above, X=H, R'. In an embodiment, R'=any group such as those described herein for R. In an embodiment, analogous polytetrazole, polytriazoles, polypyrazoles, polyimidazoles, and polypyridyls (see FIG. 1.1A) would also be suitable for SBL formation with the applicable inorganic MBB. Selection of the ligand can be based, at least in part, upon the desired inorganic MBB, and which SBL topology you want to target (e.g., sql, kgm, hcb, fes, etc.).

1) Supermolecular Building Layers (SBLs)
A) Primary Inorganic Molecular Building Blocks (MBBs) (3- or 4-Connected, Layer Forming)
i) sql and kgm (4-Connected Nodes)

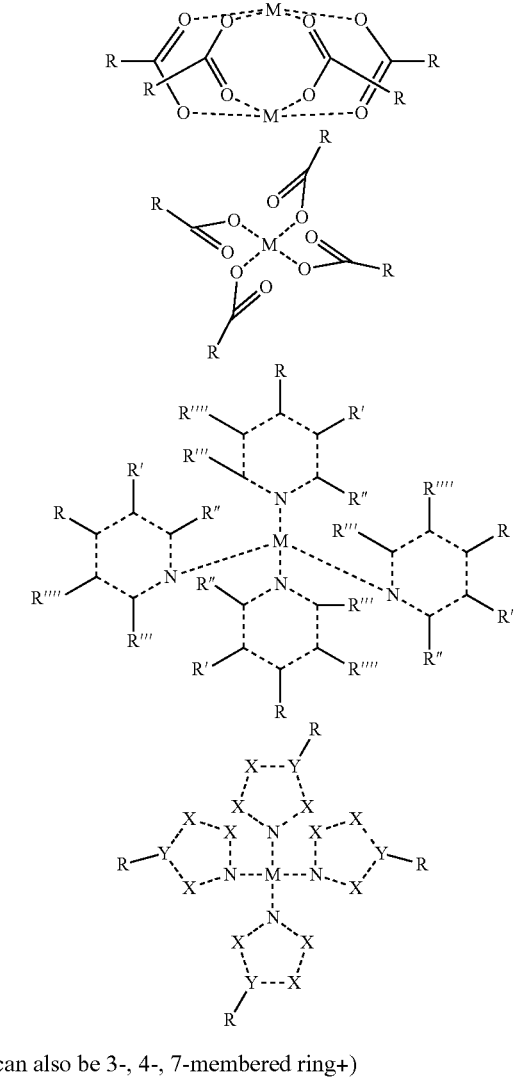

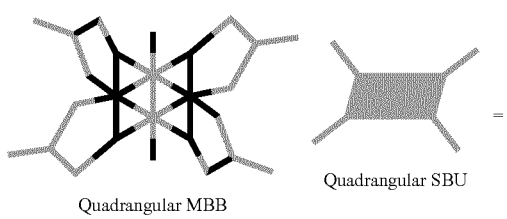

Quadrangular MBB    Quadrangular SBU

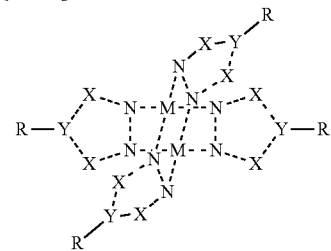

(can also be 3-, 4-, 6-, 7-membered ring+)

square/quadrangular geometry; $M^{1+}$ (e.g., Na, K, Li, Ag, etc.); $M^{2+}$ (e.g., Cu, Zn, Co, Mn, Mo, Cr, Fe, Ca, Ba, Cs, Pb, Pt, Pd, Ru, Rh, Cd, etc.); $M^{3+}$ (e.g. In, Fe, Y, Ln (Yb, Tb, etc.)); or other higher oxidative state metals such as +4, +5, +6, +7, and +8; X=C, N, NH, etc. (can have R' groups attached); Y=C, N, etc.; M-M single bond or multiple bond may exist in some examples (e.g., W, Mo, etc.) [i.e., X, Y are independently selected from carbon, nitrogen, oxygen, boron, sulfur, selenium, tellurium, silicon, phosphorus, and arsenic atoms (including cations, anions, and protonated forms thereof)]; R=H (only in the pyridyl example), any length linker such as those described herein; R'=H, any length linker such as those described herein; R'''H, any length linker such as those described herein for R [i.e., R, R', R'', and other appropriate R groups, are either generally any atom or group of atoms that do not otherwise affect the coordination of the coordinating functional group, usually a nitrogen donor (usually part of a ring) or oxygen donor (usually part of a carboxylate/carboxylic acid), or a linker moiety].

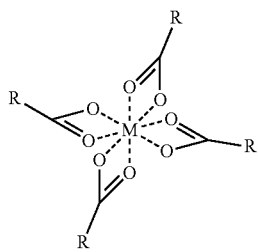

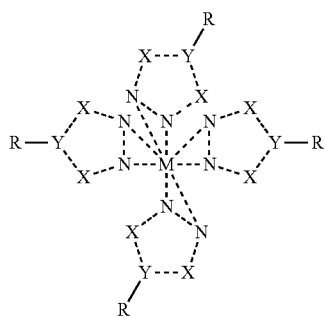

(can also be 3-, 4-, 6-, 7-membered ring+)

$M^{1+}$ (e.g., Na, K, Li, Ag, etc.); $M^{2+}$ (e.g., Ca, Ba, Cs, Pb, Cu, Zn, Co, Mn, Mo, Cr, Fe, Pt, Pd, Ru, Rh, Cd, etc.); $M^{3+}$ (e.g., Fe, In, Y, Ln (Yb, Tb, etc.)); $M^{4+}$ (e.g., Zr, Ti, V, etc.); or other higher oxidative state metals such as +5, +6, +7, and +8; X=C, N, NH, etc.; Y=C, N, etc.; R=any length linker, as described herein.

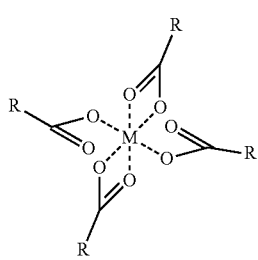

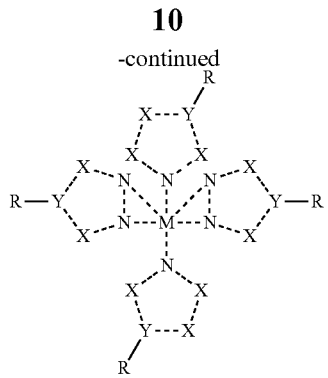

(can also be 3-, 4-, 6-, 7-membered ring+)

$M^{1+}$ (e.g., Na, K, Li, Ag, etc.); $M^{2+}$ (e.g. Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; X=C, N, NH, etc.; Y=C, N, etc.; R=any length linker, as described herein.

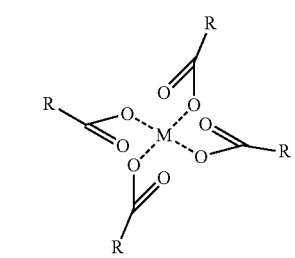

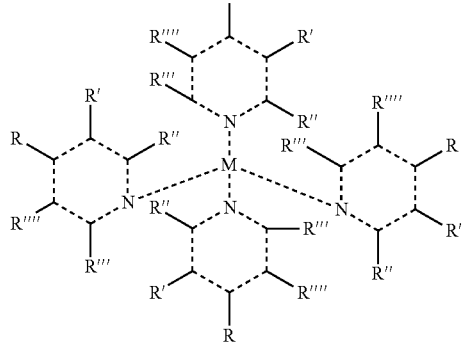

(can also be 3-, 4-, 7-membered ring+)

Tetrahedral geometry; $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; X=C, N, NH, etc.; Y=C, N, etc.; R=H (only in the pyridyl example), any length linker such as those described herein; R'=H, any length linker such as those described herein; R"=H, any length linker such as R, as described herein.
ii) hcb (3-Connected Nodes)
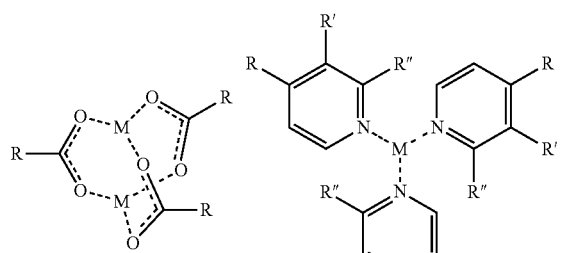
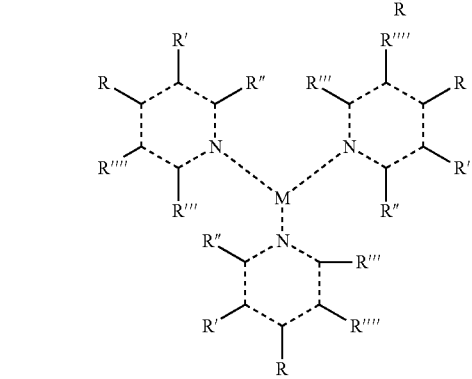
(can also be 3-, 4-, 5-, 7-membered ring+)
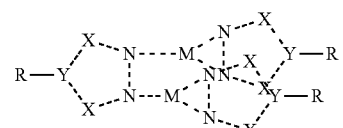
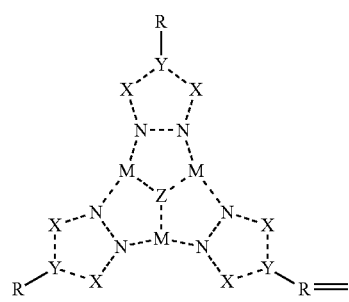
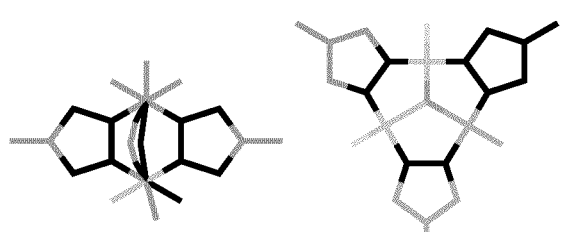
Trigonal MBB
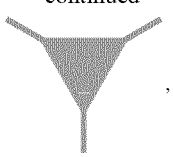
Trigonal SBU
respectively; can also be 3-, 4-, 6-, 7-membered ring+)
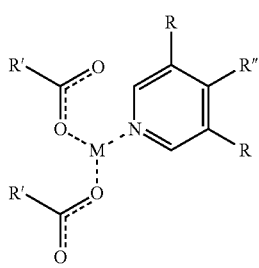
(trigonal or T-shaped geometry); e.g.,
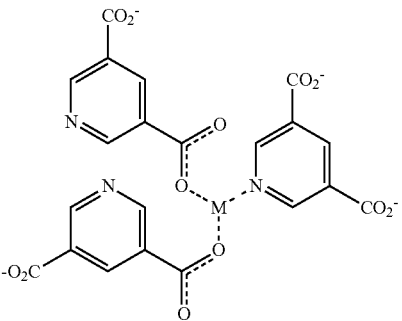
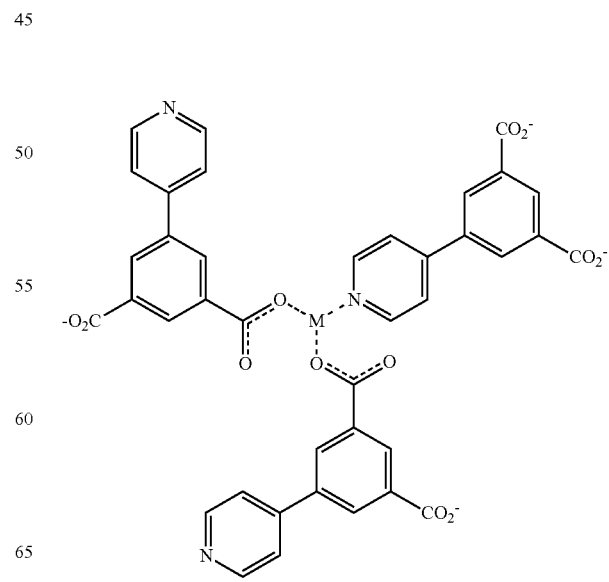

-continued

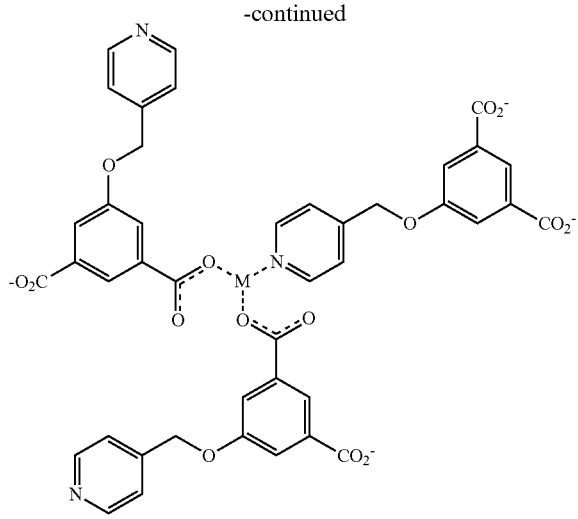

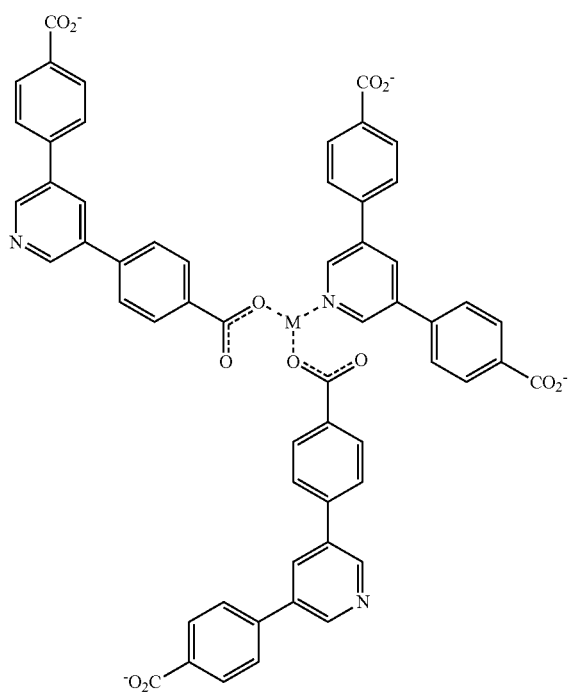

$M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; X=C, N, NH, etc.; Y=C, N, etc.; Z=O, OH, $H_2O$ N, halogen (Cl, Br, F, I), etc.; M-M single bond or multiple may exist in some examples (e.g., W, Mo, etc.); R=H (only in the polypyridyl example), any length linker, as described herein; R'=H (only in the polypyridyl example), any length linker such as those described herein R"=H, any length linker, as described herein.

B) General Ligand Design (Required to Make Layers (e.g., sql-Type, kgm-Type, hcb-Type) when Combined with the Primary Inorganic MBB(s)) for Some Embodiments In an embodiment, the rings can be monocylic, polycyclic (chain of monocyclics), or polycyclic (fused), as long as they have two potential quasi-linear coordinating functional groups. Some embodiments of ligands are described above and in FIGS. 1A and 1B.

In general, R—R""""" can be any substituent selected such that they will not adversely affect other substituents on the MBB (or the ligand subunits) and/or will not affect assembly of the SBL and/or portions of the MBB or SBL; in particular the R—R""""" substituents are preferably selected such that they do not affect the points of attachment of the MBB. Suitable substituents for R—R""""" include, for example, one or more of the following chemical moieties: —H, —OH, —OR, —COOH, —COOR, —$CONH_2$, —$NH_2$, —NHR1, —NR1R2, —SH, —SR, —$SO_2$R1, $SO_2$H, —SOR1, R1, alkyl, alkenyl, akynyl, phenyl, biphenyl, azo, and halo (including F, Cl, Br, and I), where each occurrence of R1 or R2, independently, may be hydrocarbyl or substituted hydrocarbyl (e.g., derived from: substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted aryl, or substituted or unsubstituted araalkyl).

Embodiments of the ligands are shown below:

e.g., Aromatic:

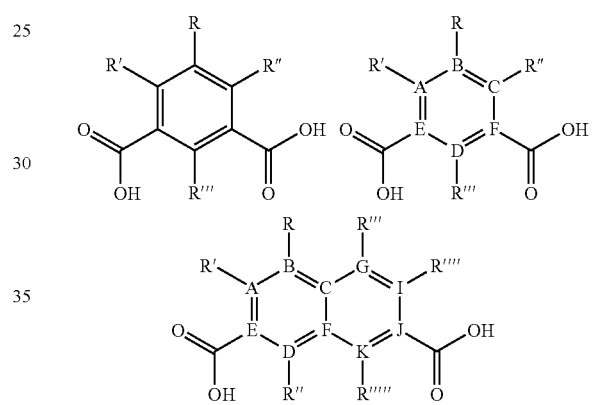

A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As;

Non-Aromatic:

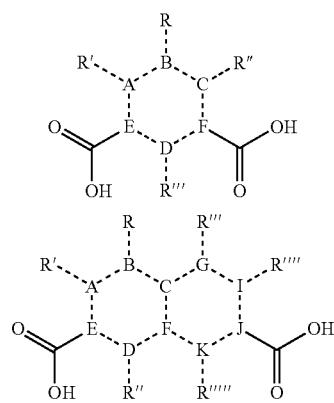

-continued

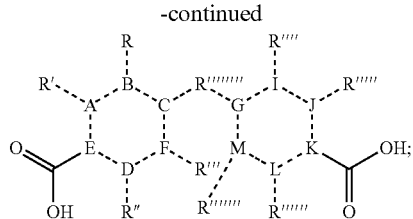

A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As; L=C, N, O, S, P, Se, Si, Te, B, As; M=C, N, O, S, P, Se, Si, Te, B, As; R′′′′′′′=alkyl, alkenyl, akynyl, phenyl, biphenyl, azo, etc.;

Aromatic or Non-Aromatic:

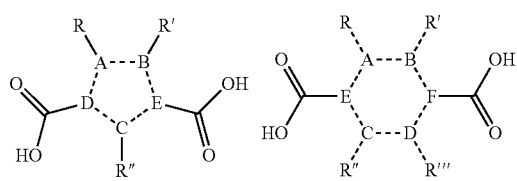

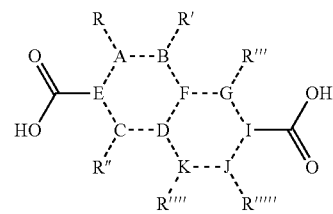

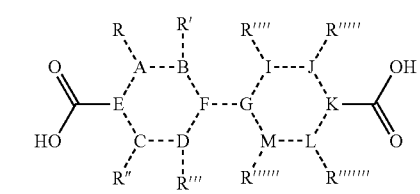

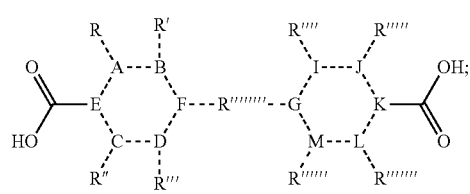

A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As; L=C, N, O, S, P, Se, Si, Te, B, As; M=C, N, O, S, P, Se, Si, Te, B, As; R′′′′′′′=alkyl, alkenyl, akynyl, phenyl, biphenyl, azo, etc.

2) Specific Ligand and Metallo-Ligand Design for Some Embodiments

A) Trigonal-Pillar (Pillared sql-MOFs, Pillared hcb-MOFs, or Pillared kgm-MOFs)

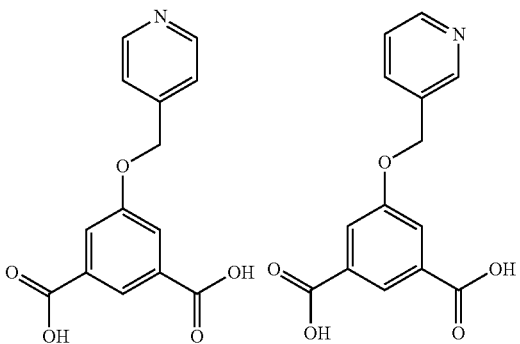

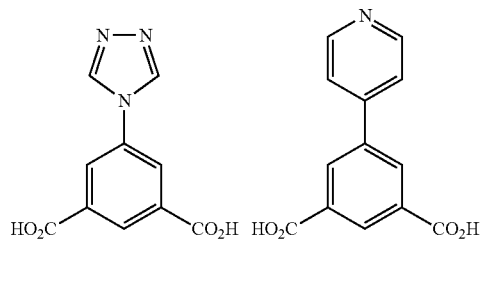

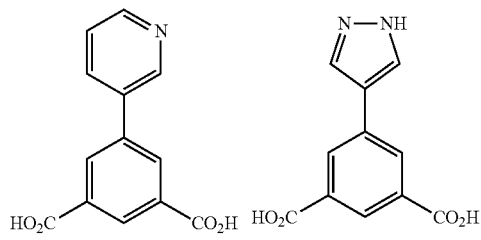

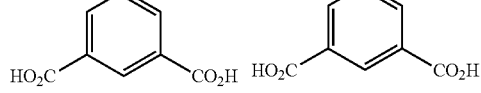

R=any length linker, as described herein

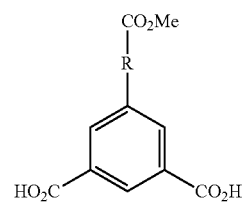

B) Quadrangular-Pillar (Pillared sql-MOFs, hcb-MOFs, Pillared kgm-MOFs)

R=any flexible, quadrangular core; e.g.,

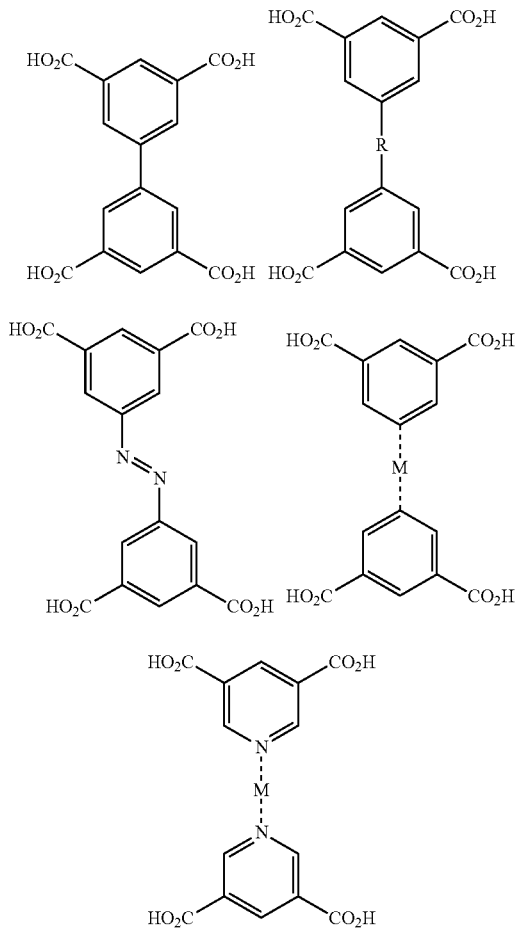

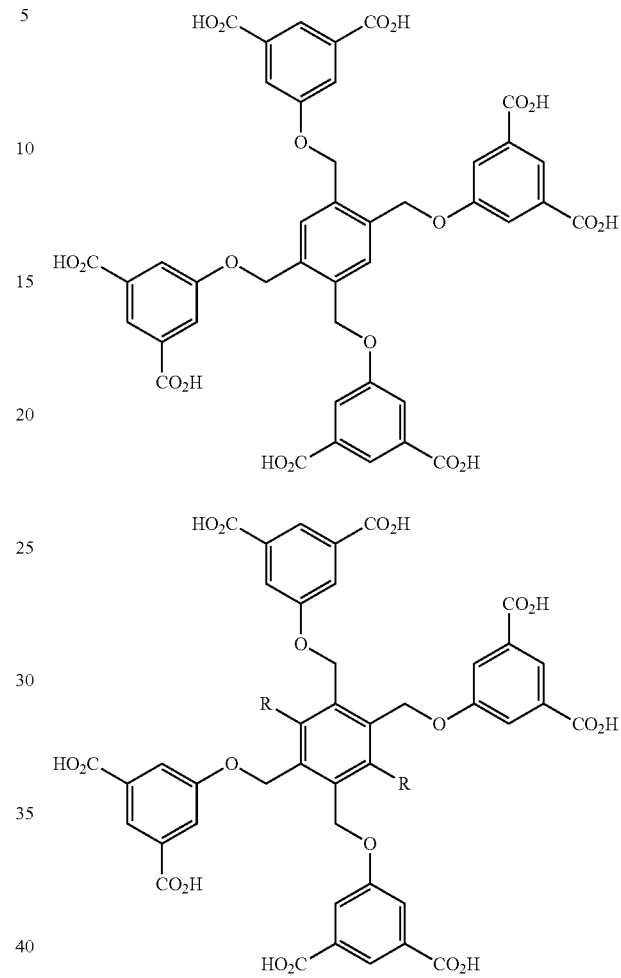

$M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; R=any length linker, as described herein.

C) Octa-Pillar (Pillared sql-MOFs)

i) Quadrangular

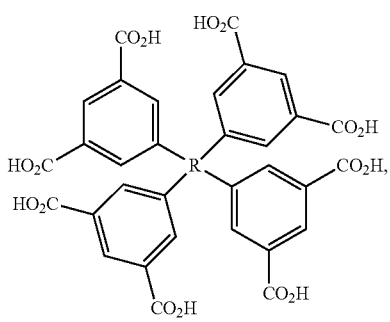

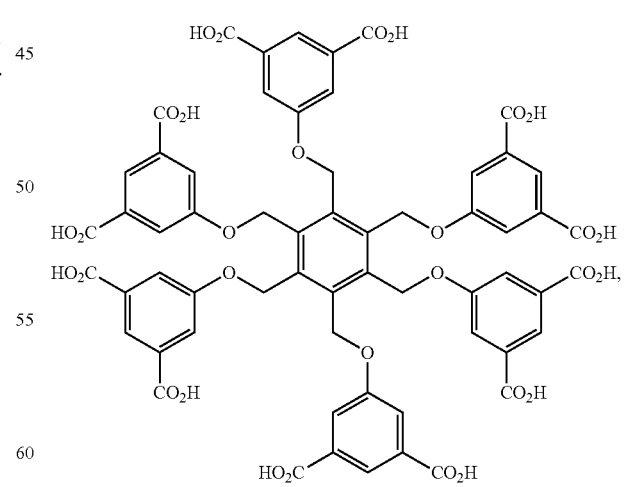

2 isophthalates or isophthalic acids free; all porphyrins and related compounds (e.g., phthalocyanines) can be metallated or not:

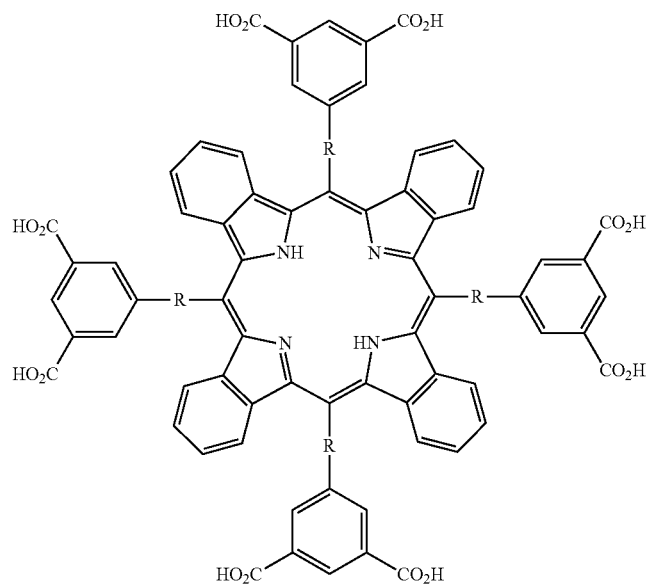
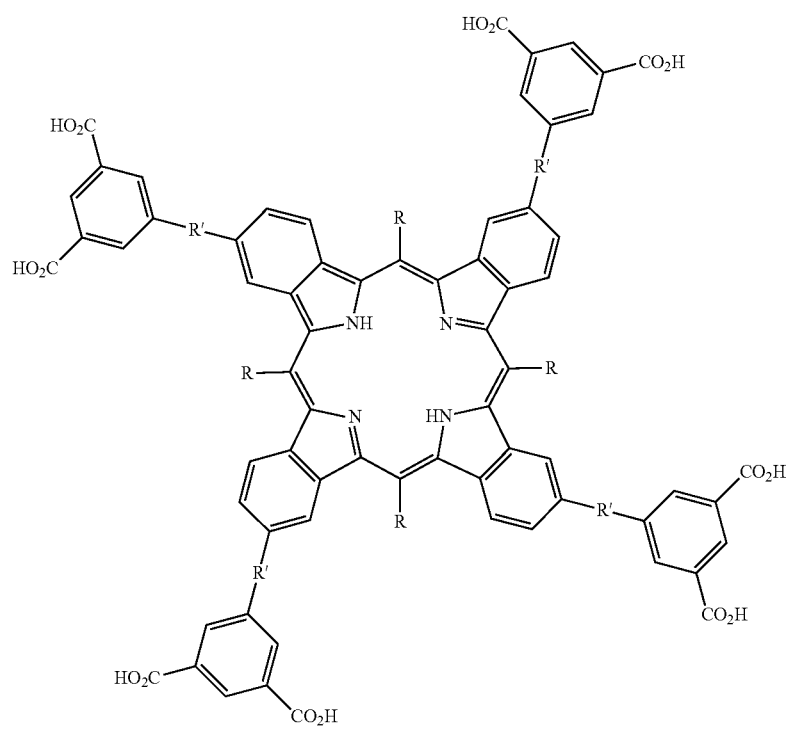

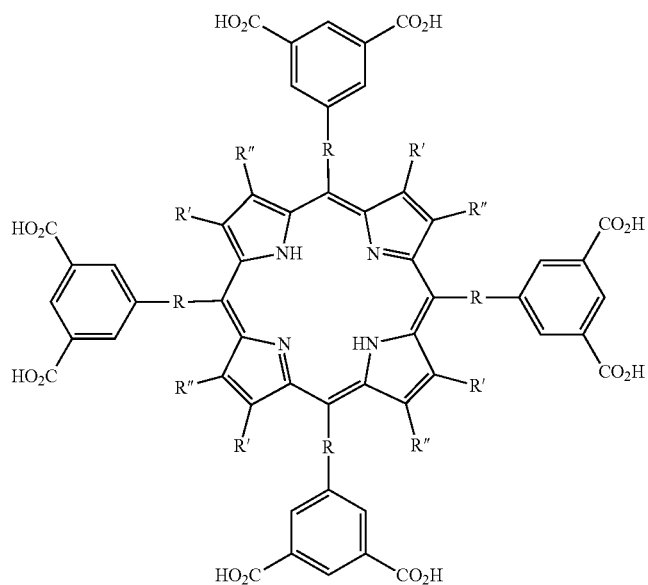
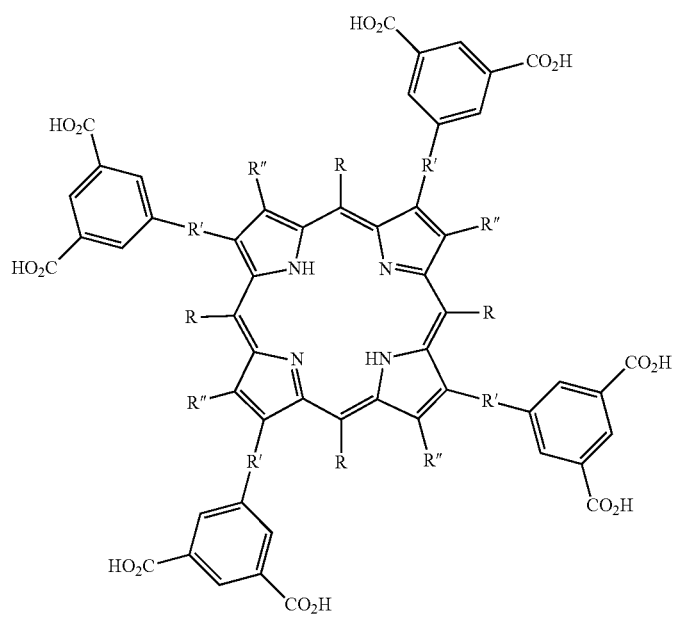
Also, metallo-ligand: paddlewheel+asymmetric tricarboxylate
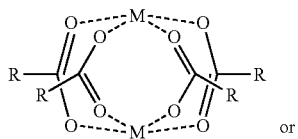 or
-continued
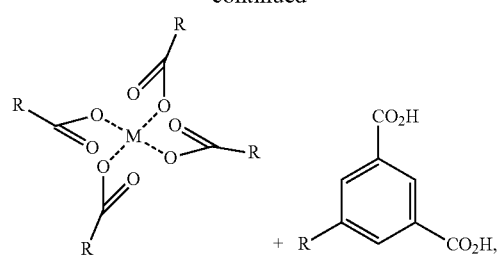

$M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; R=any length, as described herein; e.g.,
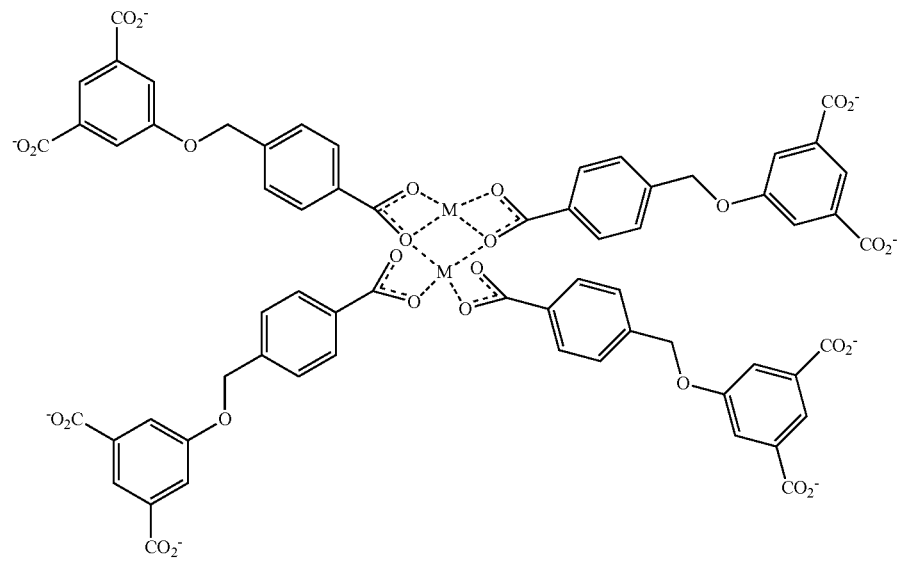
or
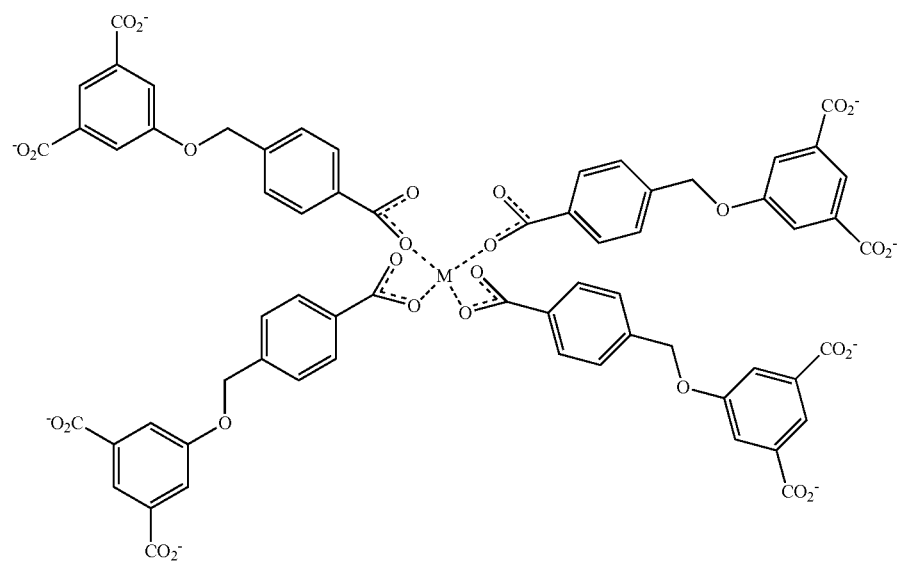

ii) Tetrahedral
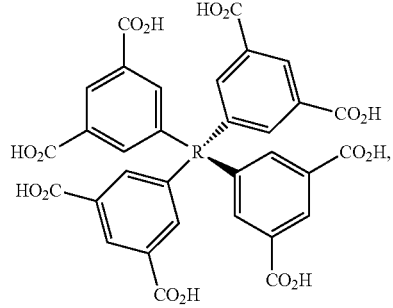
R=any flexible, tetrahedral core; e.g.,
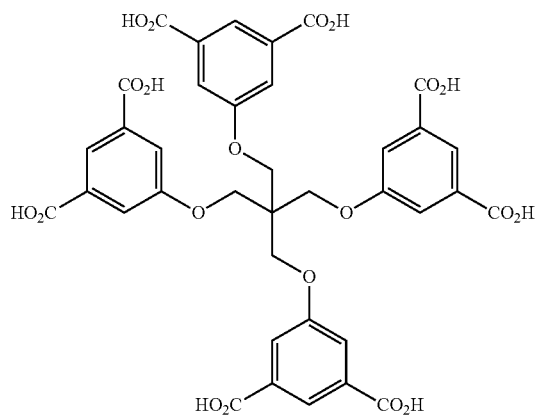
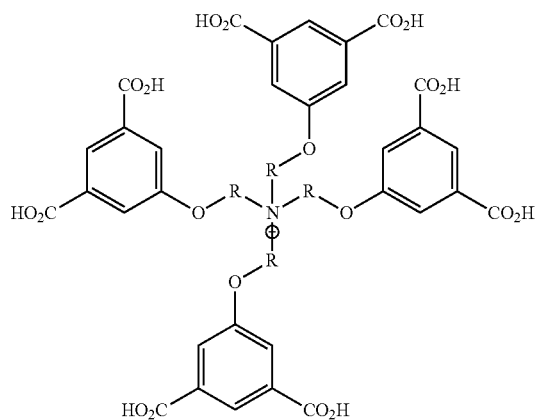
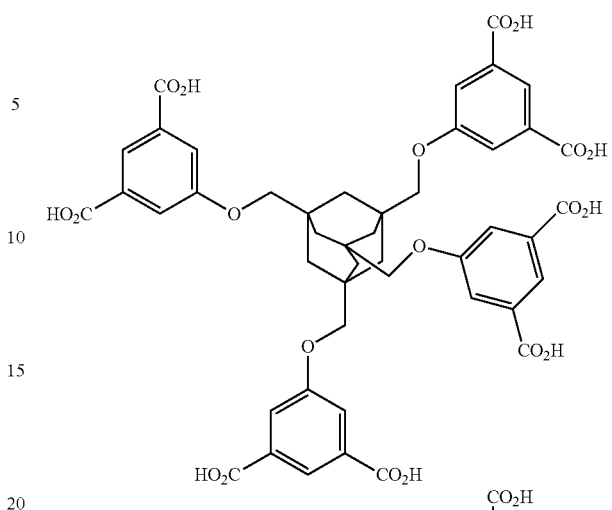
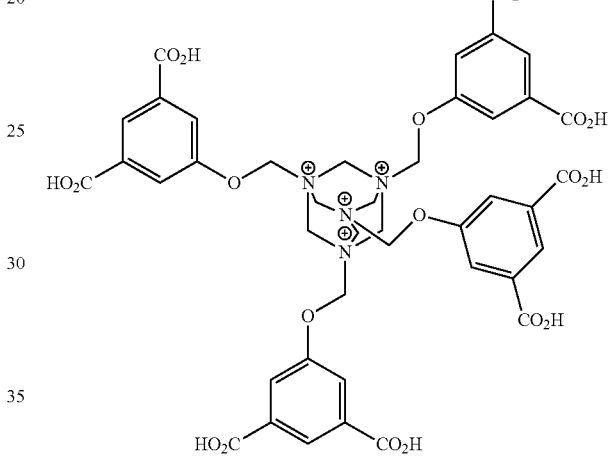
Also, metallo-ligand: tetrahedral metal+asymmetric carboxylate
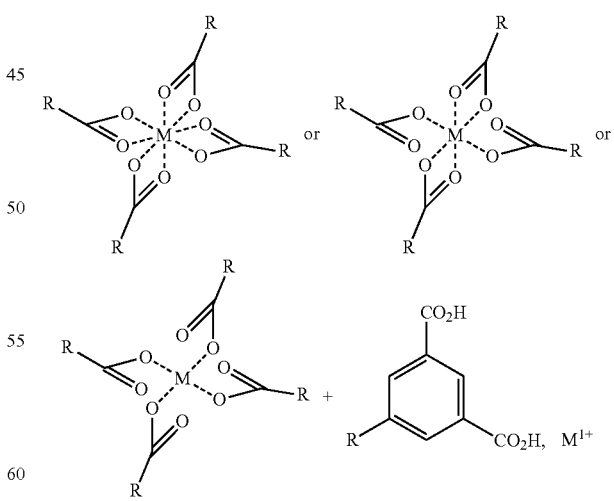
(e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; R=any length linker, as described herein; e.g.,

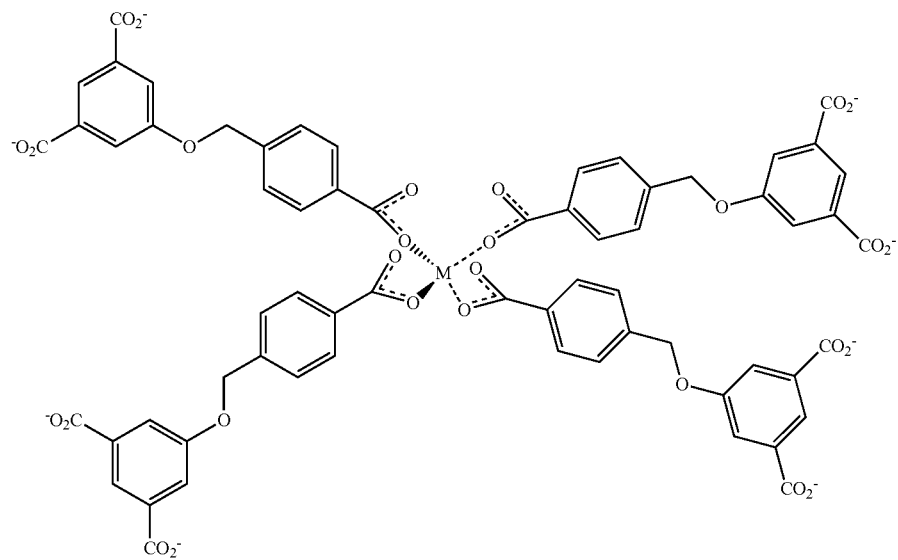
Also, metallo-ligand: tetrahedral metal+N donor
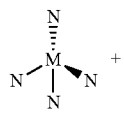
any N-donor trigonal (N-trigonal) pillar; $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; e.g.,
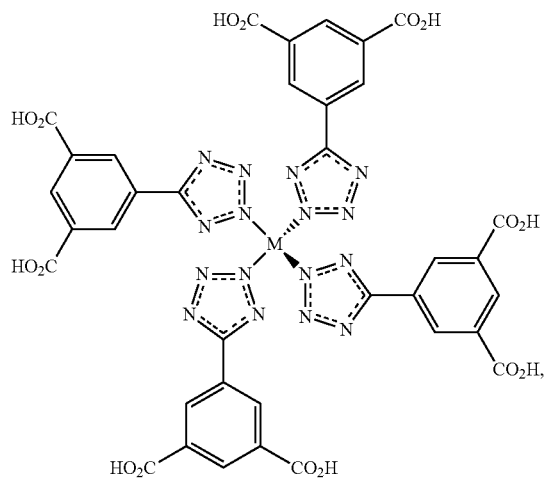
M=Y
D) Dodeca-Pillar (Pillared hcb-MOFs or kgm-MOFs)
 i) Octahedral
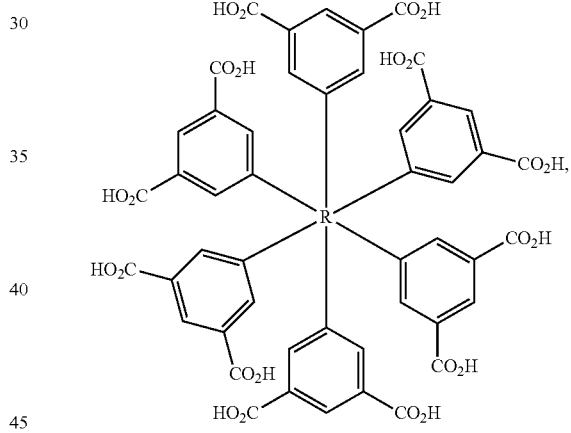
R=any octahedral core: e.g.,
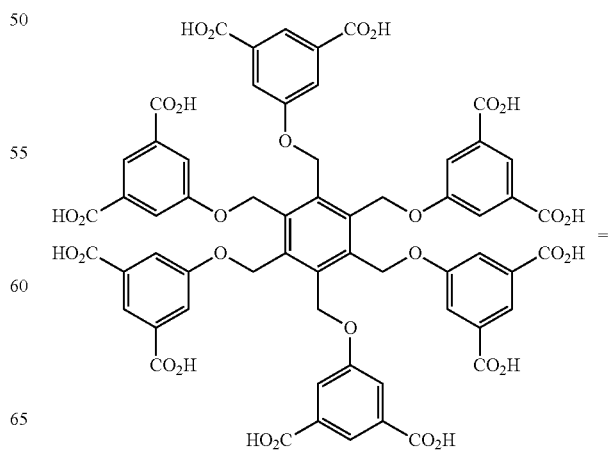

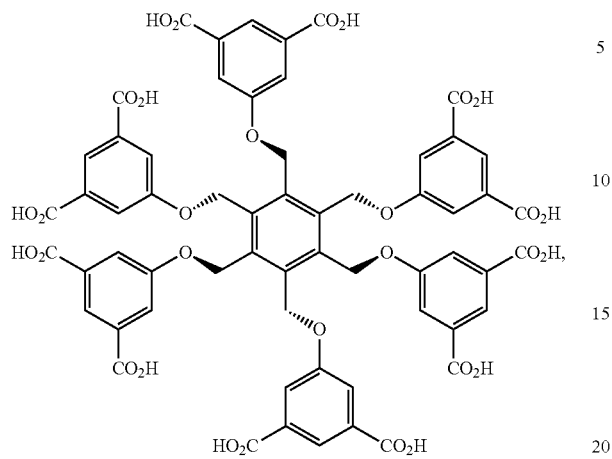
3 isophthalates up, 3 isophthalates down
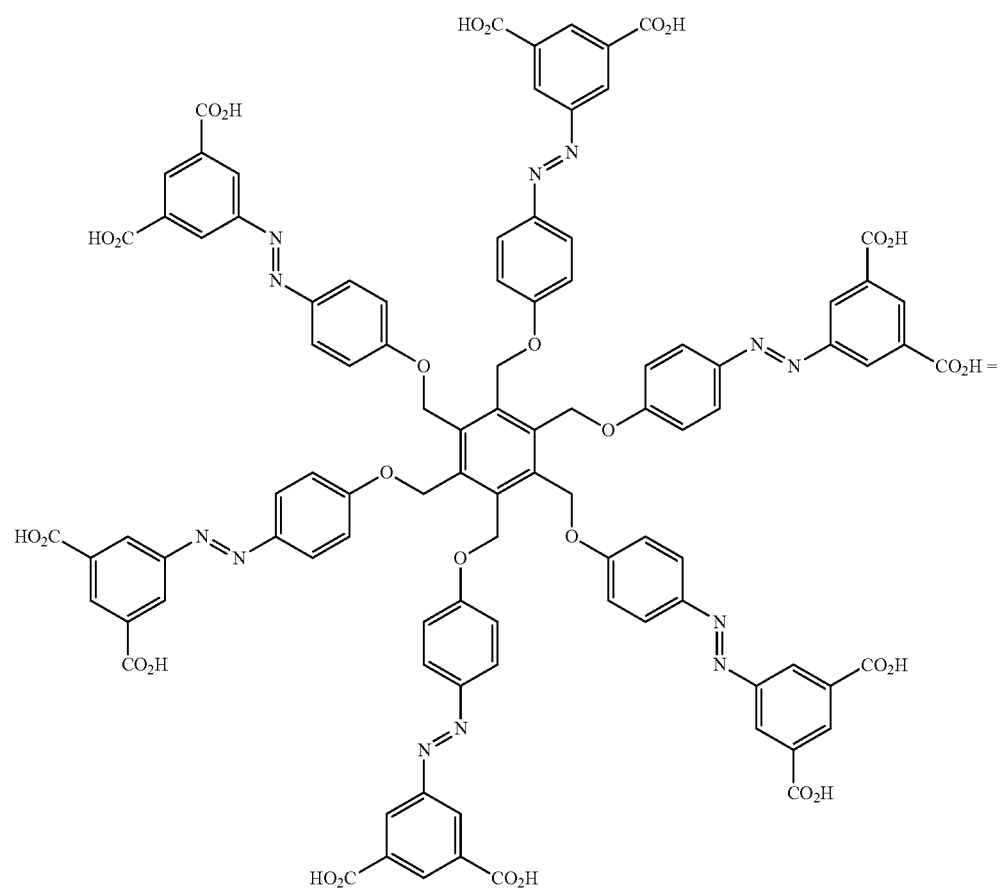

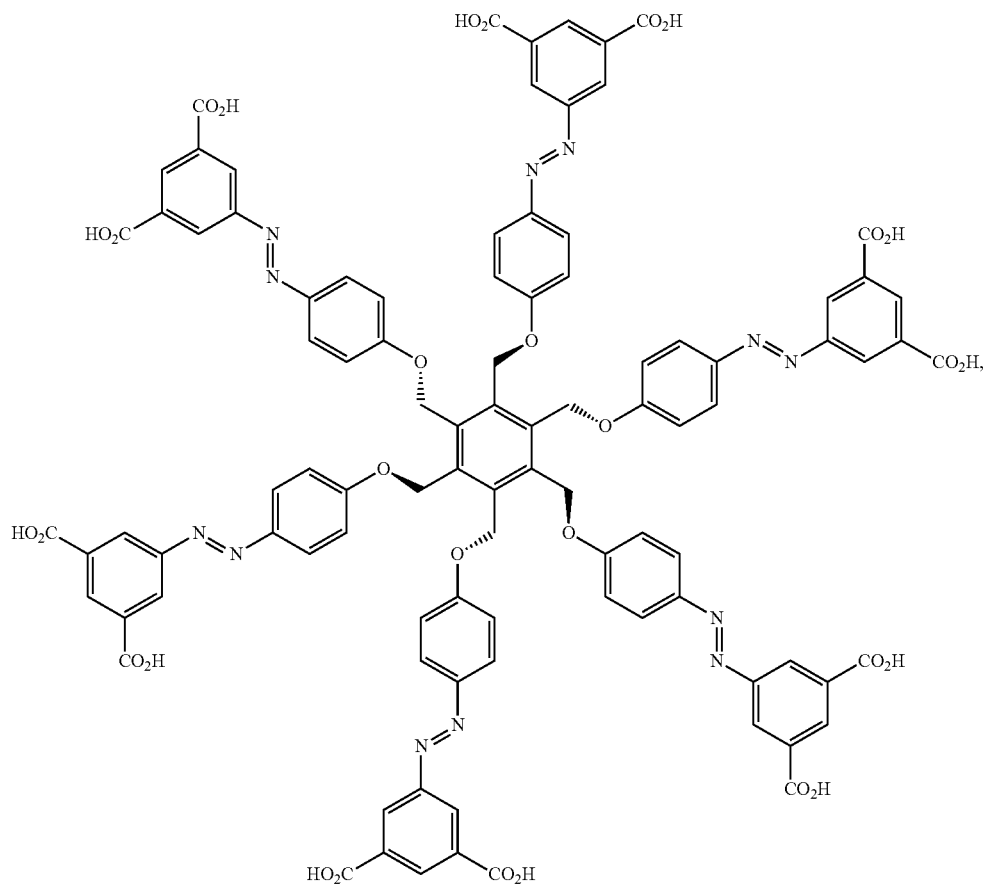
3 up, 3 down
ii) Trigonal Prism
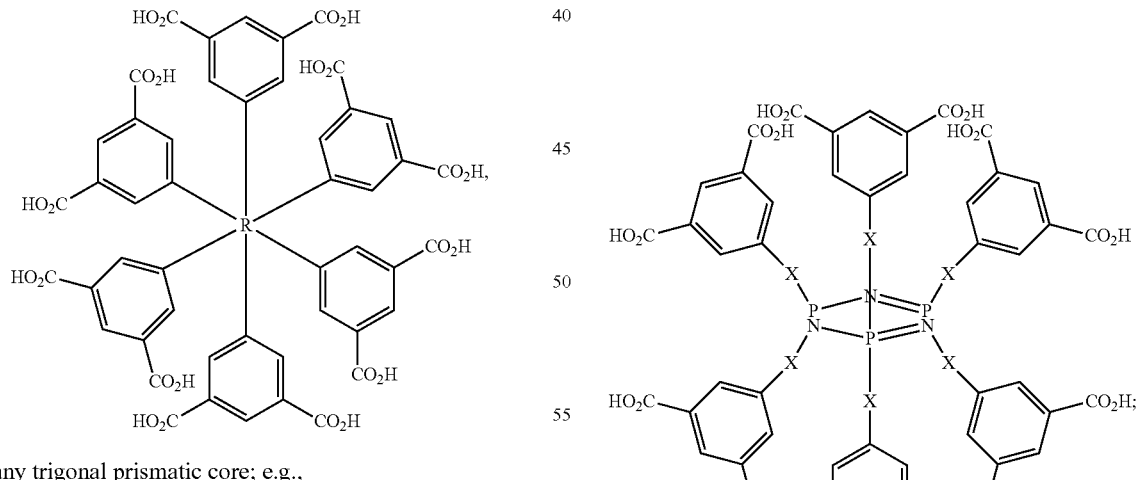
R=any trigonal prismatic core; e.g.,
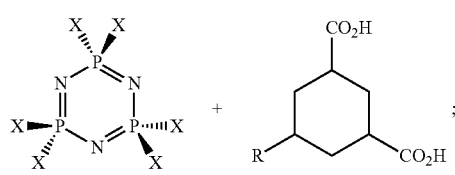
X=OR, SR, NHR; R=any length linker, as described herein; e.g.,
X=OR, SR, NHR; R=any length linker, as described herein.
Also, metallo-ligand: M₃O trimer+asymmetric tricarboxylate

33
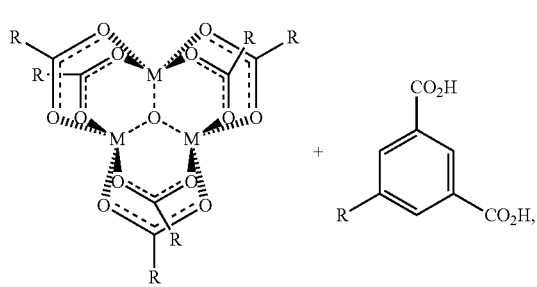
34
$M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; X═C, N, NH, etc.; Y═C, N, etc.; O═O, OH, $H_2O$ N, halogen (Cl, Br, F, I), etc.; M-M single bond or multiple may exist in some examples (e.g., W, Mo, etc.); R=any length linker, as described herein; e.g.,
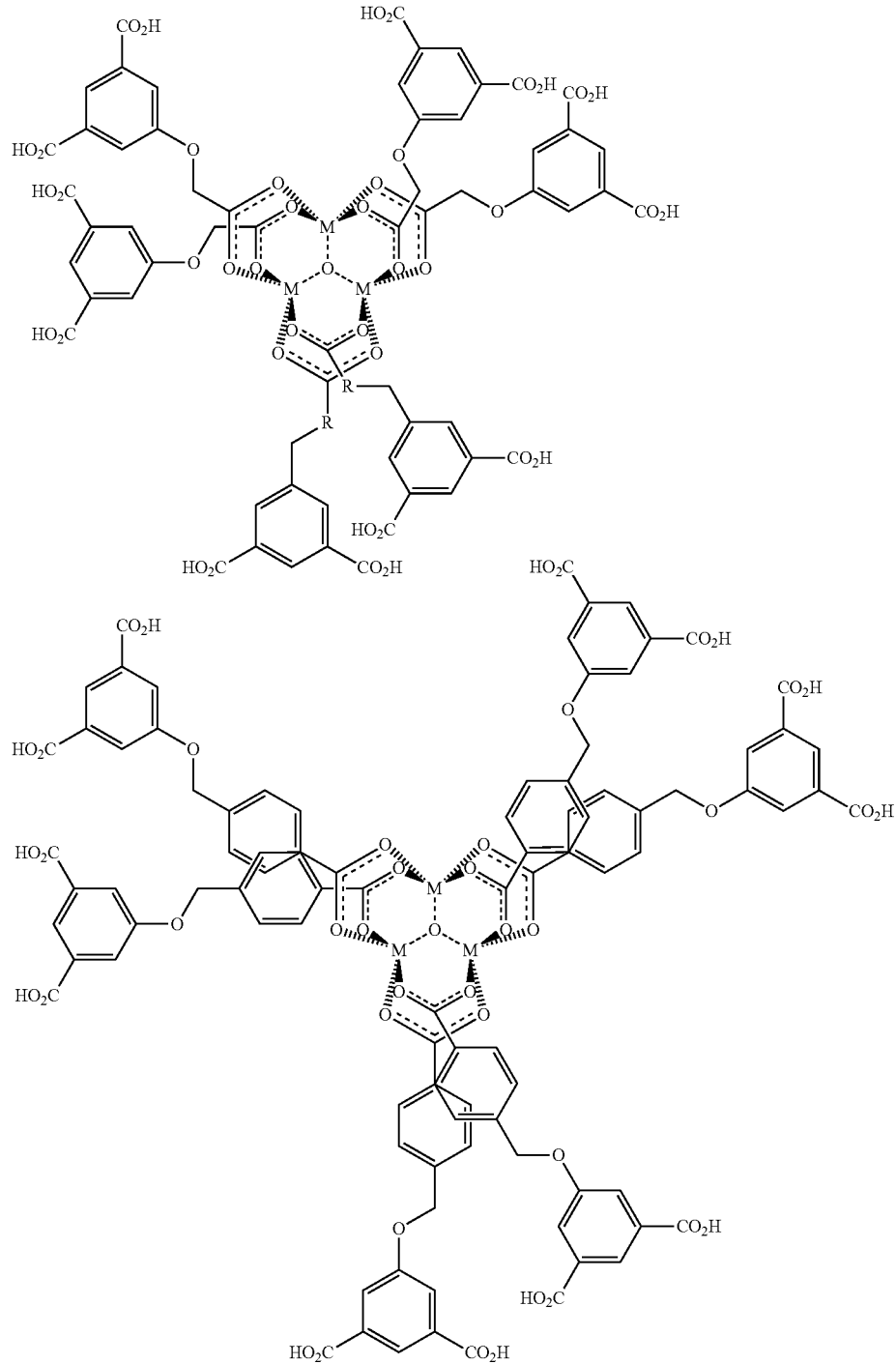

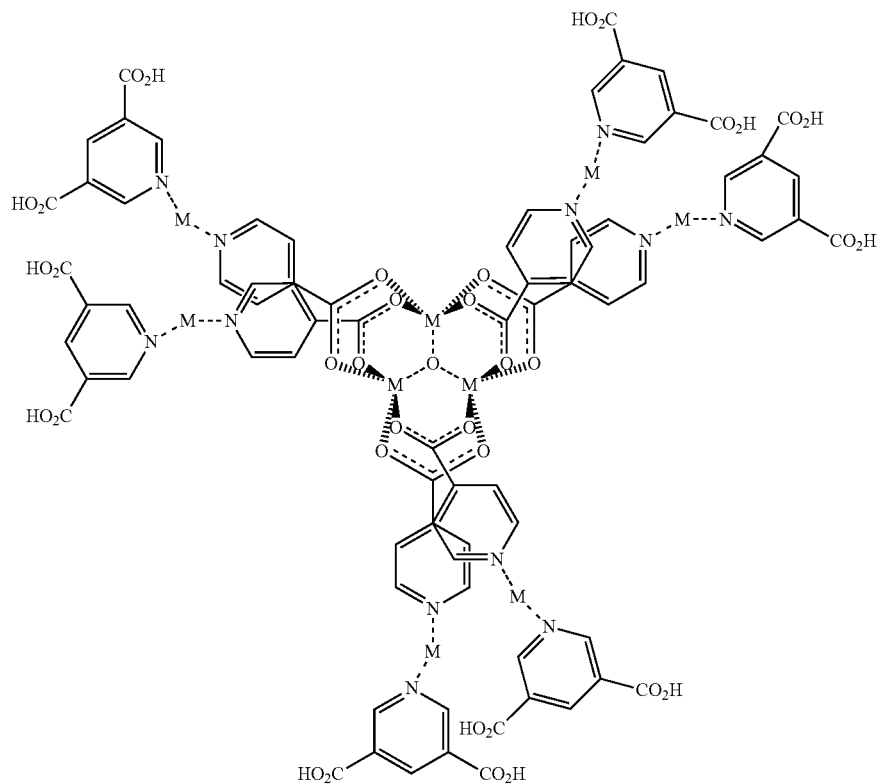

E) Hexadeca-Pillar (Pillared hcb-MOFs or kgm-MOFs)

i) Cubic

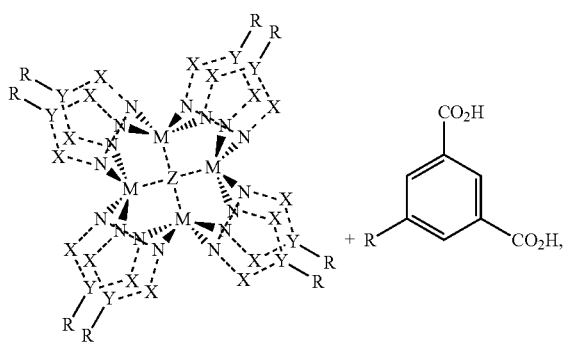

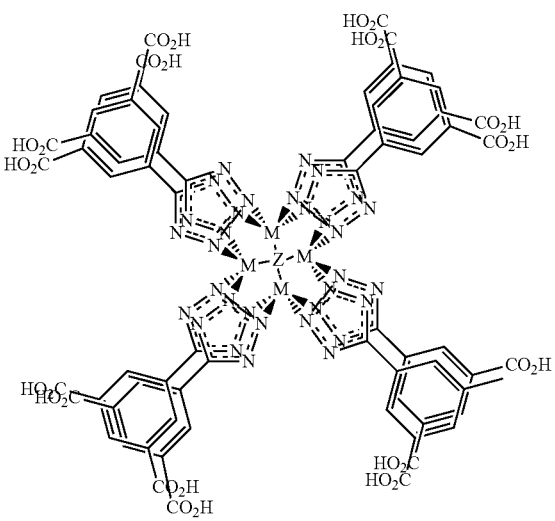

$M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.); or other higher oxidative state metals such as +5, +6, +7, and +8; X=C, N, NH, etc.; Y=C, N, etc.; Z=O, OH, $H_2O$, N, S, halogen (Cl, Br, F, I), etc.; M-M single bond or multiple may exist in some examples (e.g., W, Mo, etc.); R=any length linker, as described herein: e.g., -continued

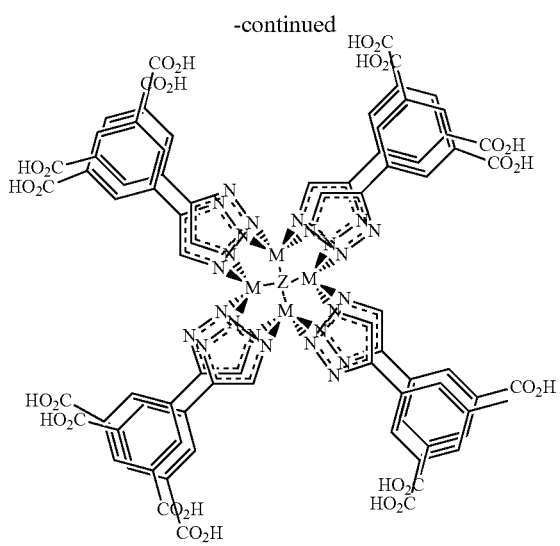

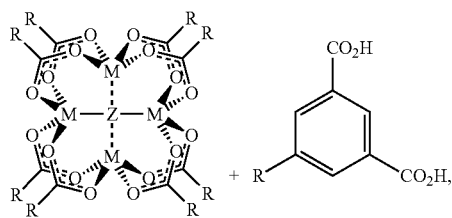

R=any length linker; M$^{1+}$ (e.g., Li, Na, K, Ag, etc.); M$^{2+}$ (e.g., Mg, Ca, Ba, Cs, Pb, Cu, Zn, Co, Mn, Mo, Cr, Fe, Pt, Pd, Ru, Rh, Cd, etc.); M$^{3+}$ (e.g., In, Fe, Y, Ln (Yb, Tb, etc.)); M$^{4+}$ (e.g., Zr, Ti, V, etc.); or other higher oxidative state metals such as +5, +6, +7, and +8; Z=O, OH, H$_2$O, N, S, halogen (Cl, Br, F, I), etc.; M-M single bond or multiple may exist in some examples (e.g., W, Mo, etc.); R=any length linker, as described herein; e.g.,

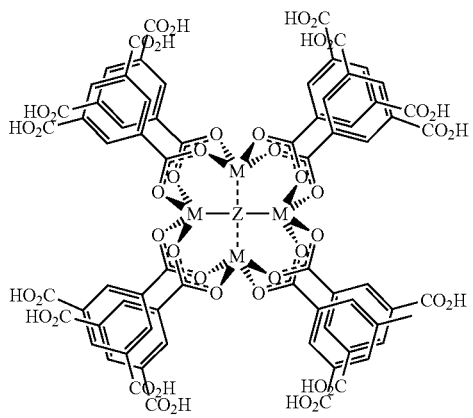

ii) Anticubic
45 degree rotation of half (e.g., upper four isophthalate termini) of the cubic MBBs Methods of making specific embodiments are provided in the Examples. These specific methods can be generally applied to other compounds described herein. A large number of chemcial assemblies, MOFs, SBLs, inorganic molecular MBBs, organic MBBs, and the like can be constructed using ligand, pillars, and hybrids of ligands and pillars that are provided herein. In an embodiment, the pore size and other dimensions of these can be designed for applications such as capturing compounds (e.g., CO$_2$), drug delivery, gas separation, and the like. Additional details are provided in the Examples.

EXAMPLE

Now having described the embodiments of the present disclosure, in general, the Examples describe some additional embodiments of the present disclosure. While embodiments of present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

FIGS. 2.1A to 2.1D describe SBL pillaring strategies and the correlation between chemical structures and simplified cartoon rendering of embodiments of the present disclosure.

FIG. 2.1A illustrates a representative 2-periodic kgm and sql layers, respectively, from in situ coordination of the building units at the left (i.e., MOF formation). FIG. 2.1B illustrates representative 2-periodic kgm-MOF and sql-MOF, respectively, based on 5-R-isophthalate bridging ligand and the latter paddlewheel MBB FIG. 2.1C illustrates representative ligand/pillar strategies that can be used to form various complexes having different layer types. Embodiments of A-A linear bifunctional ligands can bridge/pillar many types of layer (SBLs) and ligands with A-L (one axial donor and one dicarboxylate) or L-L [bis (discarboxylates)] favor sql and kgm; however, ligands with 3-fold (trigonal prismatic) or 6-fold (octahedral, which is trigonal antiprismatic) symmetry [rotational] will favor kgm, while ligands with 4-fold (quadrangular or tetrahedral) or 8-fold (cubic or anticubic) symmetry will favor sql.

FIG. 2.1D illustrates a rendering showing the concept of "pillaring" the 2D MOF layers (SBLs).

Example 2

Brief Introduction:
A new pillaring strategy, based on a ligand-to-axial approach that combines the two previous common techniques, axial-to-axial and ligand-to-ligand, and permits design, access, and construction of higher dimensional MOFs, is introduced and validated. Trigonal heterofunctional ligands, in this case isophthalic acid cores functionalized at the 5-position with N-donor (e.g., pyridyl- or triazolyl-type) moieties, are designed and utilized to cross-link pre-targeted two dimensional layers, namely edge transitive Kagomé and square lattices, into predicted three-dimensional MOFs with tunable large cavities, resulting in isoreticular platforms.

Discussion:
Metal-organic frameworks (MOFs) is an emerging class of porous solid-state materials with significant contributions in numerous application areas including, but not limited to, catalysis, separations, gas storage, and drug delivery.[1] In this typical class of periodic solids, there has been great progress toward design, due largely to the ability to target specific [molecular] building blocks with given geometry and directionality (e.g. squares, tetrahedra, etc.) prior to the assembly process.[2] One of the most common examples, likely owing to its ability to form with a large range of metals, is the $M_2(O_2CR)_4A_2$ paddlewheel-like unit (FIG. 3.1).[2-4] This dinuclear cluster can serve as (i) a simple linear bridge when the carboxylates terminate the dimer (i.e. monocarboxylates) and polytopic ligands coordinate through the axial or apical (A) sites, (ii) a square building unit if the carboxylate C atoms serve as sole points of extension (i.e. terminal axial ligands), and (iii) an octahedral building unit, if all the dimer cluster coordination sites are occupied by polytopic ligands (i.e. saturated).[1,4]

It is recognized that, for square building units, there are only two edge transitive 2D nets, square lattice (sql) and Kagomé lattice (kgm).[5] The predictability and regular formation of the square paddlewheel molecular building block (MBB) has allowed the design and synthesis of several MOFs based on these network topologies, where, for example, the MOF layer is composed of $M_2(O_2CR)_4(A)_2$ dimer units bridged by linear or bent dicarboxylate organic ligands (e.g. terephthalate or isophthalate, respectively) (FIG. 3.2), and the layers are separated by terminal axial ligands (A) and/or guest molecules.[3d,e]

Recently, there has been an increased effort to generate 3D porous MOFs via "pillaring" these layered MOFs.[6-7] One approach, referred to here as axial-to-axial (A-A) pillaring, takes additional advantage of the auxiliary axial metal sites of the paddlewheel, which are typically occupied by terminal ligands like water or pyridine. In this case, pairs of terminal ligands are replaced by a ditopic (bridging) ligand, typically a nitrogen donor like pyrazine or 4,4'-bipyridine (bipy), that can coordinate the axial positions of two dimer units from neighboring layers (FIG. 3.2) resulting in bridged (i.e. cross-linked or pillared) MOF layers based on six-connected dimer units (i.e., a 6-connected octahedral-based 3D MOF).[6]

Another, albeit more recent, pillaring method involves what we call ligand-to-ligand (L-L) pillaring, where specific ligands are selected to simultaneously contain two bridging ligand moieties (e.g., di-isophthalates, "X"- or "T"-shaped) that pillar adjacent layers through the covalent linkage of the tetracarboxylate ligand (FIG. 3.2). When the 4-connected ligand coordinates to form the 4-connected paddlewheel MBB, the resulting 3D MOF is based on a (4,4)-connected topology (e.g., nbo-MOFs).[7]

Here, we present a strategy, henceforth referred to as ligand-to-axial (L-A) pillaring. It is expected that a multi-functional ligand simultaneously containing carboxylate and nitrogen donor (or similar) moieties,[8] when coordinated with the expected paddlewheel MBB, will lead to a 3D structure. Specifically, each ligand is selected/designed to be bifunctional and trigonal, containing the ditopic bridging moiety (e.g., 5-substituted isophthalate) that forms the expected MOF layer (i.e., kgm and sql),[9] as well as a second function (e.g., an N-donor group in the 5-position) to coordinate the apical metal site of an MBB in a neighboring layer. This trigonal (3-connected) pillaring technique will produce an octahedral-like MBB (6-connected building unit, FIG. 3.1), and thus results in the construction of (3,6)-connected 3D MOFs.[10]

A survey of the RCSR data base[5] reveals twenty possible (3,6)-connected nets[11], only six of which (i.e., anh, ant, apo, brk, pyr, rtl), to our knowledge, can be deconstructed into 2D layers of octahedra linked by triangles ("Y"- or "T"-shaped). As such, these networks would be regarded as the most plausible targets using our strategy, since the 2D layers in each correspond to the edge transitive sql network and edge transitive nets are the most appropriate targets in crystal chemistry.[12] It should be noted, there are no (3,6)-connected nets in the RCSR database composed of triangle-linked edge transitive kgm 2D sheets, which would be essential to determine the corresponding pillared kgm-MOF. However, to our knowledge there has been only one such (3,6)-connected net, $ScD_{0.33}$ (46032),[13] reported in the TOPOS Topological Database (TTD), which should serve as a suitable target. As expected, reactions between selected hetero-, bi-functional trigonal ligands (FIG. 3.3) and various metal salts have afforded the predicted 3D MOFs based on pillaring of the 2D edge transitive nets, sql and kgm.

According to O'Keeffe, et al.,[10b] the rutile net (rtl) is likely the "easiest target for a designed synthesis" for combining triangles and octahedra, which is supported by its relatively large occurrence in MOFs compared to other (triangle, octahedra)-based (3,6)-connected topologies.[4,13] In addition, the rtl net is one of the nets that can be regarded as square grids (sql) pillared by triangular (3-connected) nodes. Thus, the rtl net is a suitable target for constructing 3D MOFs from our triangular ligands when combined with the paddlewheel octahedral building unit.

Indeed, 5-(4H-1,2,4-triazol-4-yl)isophthalic acid ($H_2L1$) reacts with copper nitrate to form a L-A pillared sql-MOF, Cu(L1).xsolv (1), based on non-equilateral triangles pillaring 2D layers of octahedra (FIG. 3.4). This ligand-to-axial pillared sql-MOF also can be viewed as a 3D MOF, where L1 serves as a 3-connected node and the paddlewheel cluster as a 6-connected octahedral node. Topological analysis of the resultant (3,6)-connected net reveals 1 is the expected rtl-MOF.[5]

The 1,3-BDC moieties form sql-MOF sheets in 1,2-alternate fashion,[14] where a pair of adjacent benzenes in any given four-member ring point up while the other adjacent pair point down. This orientation results in the alignment of quadrangular windows of each 2D sql-MOF sheet, exposing channels (~6.2 Å×9.6 Å) running along the c-axis. The calculated total potential solvent accessible volume for the as-synthesized 1, upon removal of guest solvent molecules, was estimated at 970.7 Å$^3$ per unit cell volume (1764.0 Å$^3$) or 55.0% v/v.

Reaction between copper nitrate and 5-(4-pyridinyl-methoxy)-isophthalic acid ($H_2L2$) results in the expected L-A pillared kgm-MOF, Cu(L2).xsolv (2) (FIG. 3.5), which can also be viewed as a 3D MOF, where L2 serves as a 3-connected node and the paddlewheel cluster as a 6-connected octahedral node. Topological analysis[5] reveals that 2 is consistent with the anticipated $ScD_{0.33}$ (46032),[13] a novel network in MOF chemistry.

The kgm-MOF sheets in 2 are pillared in an arrangement where pairs of three-member ring windows of neighboring sheets are separated by six-member ring windows (i.e. 3, 3, 6, 3, 3) to give repeating hourglass-shaped channels (FIG. 3.5c). These hourglass-shaped channels result in two types of cavities (~7.8 Å and 12.6 Å diameters), one between neighboring three-member rings and one in the hexagonal windows between neighboring three-member ring windows, as shown in FIG. 3.5c. The calculated total potential solvent accessible volume for the as-synthesized 2, upon removal of guest solvent molecules, was estimated at 6969.1 Å$^3$ per unit cell volume (11888.4 Å$^3$) or 58.6%.

As expected, reaction between copper nitrate and the L2 isomer, 5-(3-pyridinylmethoxy)-isophthalic acid ($H_2L3$), results in an analogous L-A pillared kgm-MOF, Cu(L3).xsolv (3). The orientation of the ligands results in slight changes in cavity shape and size (~8.3 Å and 12.0 Å diameters). The calculated total potential solvent accessible volume for the as-synthesized 3, upon removal of guest solvent molecules, was estimated at 5471.2 Å$^3$ per unit cell volume (10204.0 Å$^3$) or 53.6% v/v.

There are five other (3,6)-connected nets based on the assembly of triangles linking 2D layers of octahedra. Accordingly, just as the parent mineral $TiO_2$ adopts several (3,6)-connected polymorphic forms (e.g. ant, apo, brk, and rtl), multiple rutile-like (i.e. trigonal-pillared sql) polymorphs should be anticipated here. A ligand lower in symmetry and flexible in nature should allow for the formation of these less regular nets.

Slight modification of the reaction conditions between copper nitrate and $H_2L2$ results in another type of pillared sql-MOF, Cu(L2).xsolv (4). Adding a small amount of water to the reaction conditions resulted in a mixture of crystals of 2 and 4, but the addition of a structure-directing agent, in this case 1-iodo-4-nitrobenzene, leads to pure 4. This ligand-to-axial pillared sql-MOF also can be viewed as a 3D MOF, where the L2 ligand serves as a 3-connected node and the paddlewheel cluster as a 6-connected octahedral node (FIG. 3.6). Topological analysis of the resultant (3,6)-connected net reveals that 4 is one of the expected structures, an apo-MOF;[5] to our knowledge, this is the first example of successfully targeting such frameworks.

As in the previous L-A pillared sql-MOF, the sql sheets are formed via the 1,3-BDC moiety (1,2-alternate fashion[14]) of the ligand, L2, and the nitrogen (pyridinyl) moiety (of L2) coordinates to the axial positions of the metal-carboxylate paddlewheel clusters (FIG. 3.6). However, in this case the orientation results in the quadrangular windows (~8.4 Å×9.8 Å) of each 2D sql-MOF sheet being staggered between neighboring sheets, exposing zigzag channels (~6.8 Å×6.8 Å) running along the c-axis. The calculated total potential solvent accessible volume for the as-synthesized 4, upon removal of guest solvent molecules, was estimated at 2715.5 Å$^3$ per unit cell volume (4634.0 Å$^3$) or 58.6% v/v.

The unique nature of these nets and the resultant cavities makes them amenable to isoreticular chemistry, allowing the design and synthesis of expanded (3,6)-connected MOFs from an infinite number of trigonal ligands (e.g. interlayer distance of ~10.884 Å in 1 vs. ~13.663 Å in 4, and ~12.8 Å in 2 vs. ~11.8 Å in 3) and/or functionalized (e.g. triazolyl in 1 vs. pyridinyl-alkoxy in 2-4)). The judicious choice of ligands with different lengths and/or functionalities will permit the construction of desired structures with tunable cages/pores of assorted sizes and functionalities for targeted applications. To validate this strategy, we synthesized an organic ligand analogous to $H_2L2$, both extended (i.e. longer, ~18 Å) and functionalized (i.e. azo moiety), 5-[(1E)-2-[4-(4-pyridinyloxyl)phenyl]diazenyl]-isophthalic acid ($H_2L4$) (FIG. 3.3d), and then reacted $H_2L4$ with copper nitrate in DMF, which produced small green hexagonal-plate crystals. From the single-crystal X-ray diffraction data, we were able only to determine the unit cell (R-3, a=18.5 Å, c=48.6 Å), which corresponds to the expected isoreticular (expanded)L-A trigonal-pillared kgm-MOF, Cu(L4).xsolv (5). Comparison between the experimental and simulated PXRD patterns supports the formation of the desired expanded/functionalized L-A pillared kgm-MOF. From the simulated structure of 5, we estimate an interlayer distance of 21.6 Å, with a calculated total potential solvent accessible volume for estimated at 8950.7 Å$^3$ per unit cell volume (14404.9 Å$^3$) or 62.1% v/v.

Here we have presented a new strategy for the design and access of isoreticular 3D MOF materials using select hetero-, bifunctional trigonal ligands, which combines and complements existing pillaring techniques for layered (2D) MOFs. We have successfully utilized this approach to synthesize predicted (3,6)-connected MOFs based on a series of trigonal ligand (3-connected) pillars and the common/expected $M_2(O_2CR)A_2$-based MOF layers, where the paddlewheel MBB serves as an octahedral node (6-connected). This route results in easily targeted MOFs with large channels and cavities that are readily fine-tunable based on simple organic ligand manipulation and metal ion selection, which, by default, implies they are excellent candidates as suitable platforms for MOF applications. Sorption, encapsulation, and further isoreticulation (expansion/functionalization) and crystallographic studies are currently underway.

REFERENCES, each of which is incorporated by reference
(1) *Metal-Organic Frameworks: Design and Application*; L. MacGillivray, Ed.; WILEY-VCH Verlag GmbH & Co. KGaA: Weinheim, 2010.
(2) Tranchemontagne, D. J.; Mendoza-Cortes, J. L.; O'Keeffe, M.; Yaghi, O. M. *Chem. Soc. Rev.* 2009, 38, 1257-1283.
(3) (a) *Multiple Bonds between Metal Atoms*; F. A. Cotton, C. A. Murillo, R. A. Walton, Eds.; Springer Science and Business Media, Inc.: N.Y., 2005. (b) Cotton, F. A.; Lin, C.; Murillo, C. A. *Acc. Chem. Res.* 2001, 34, 759-771. (c) Furukawa, H.; Kim, J.; Ockwig, N. W.; O'Keeffe, M.; Yaghi, O. M. *J. Am. Chem. Soc.* 2008, 130, 11650-11661. (d) Eddaoudi, M.; Kim, J.; Vodak, D.; Sudik, A.; Wachter, J.; O'Keeffe, M.; Yaghi, O. M. *Proc. Natl. Acad. Sci. USA*. 2002, 99, 4900-4904. (e) Kim, J.; Chen, B.; Reineke, T. M.; Li, H.; Eddaoudi, M.; Moler, D. B.; O'Keeffe, M.; Yaghi, O. M. *J. Am. Chem. Soc.* 2001, 123, 8239-8247.
(4) Allen, F. H. *Acta Cryst.* 2002, B58, 380-388 (CSD): (3,6)-connected (105 rtl, 23 pyr, 20 ant, 16 apo, 0 brk, unknown anh).
(5) O'Keeffe, M.; Peskov, M. A.; Ramsden, S. J.; Yaghi, O. M. *Accts. Chem. Res.* 2008, 41, 1782-1789. The vertex symbols [(4.6$_2$.6$_2$)(4.4.6.6.6.6.6.6.6.6.6$_2$.6$_2$.*.*.*)] and coordination sequences (3, 14, 19, 62, 51, 144, 99, 254, 163, 400 and 6, 10, 38, 34, 102, 74, 198, 130, 326, 202, respectively) of 1 match the rtl topology. The vertex symbols [(4.4.6)(4.4.4.4.6.6.8$_2$.8$_2$.8$_2$.8$_2$.8$_4$.8$_4$.12$_8$.12$_{16}$.12$_{16}$)] and coordination sequences (3, 13, 15, 50, 45, 124, 90, 229, 150, 358 and 6, 8, 30, 30, 90, 68, 180, 126, 300, 180, respectively) of 2 and 3 are not known in the RCSR. The vertex symbols [(4.6$_2$.6$_2$)(4.4.6.6.6.6.6.6.6$_2$.6$_2$.6$_2$.8$_5$.*.*.*)] and coordination sequences (3, 14, 19, 62, 53, 148, 103, 262, 171, 416 and 6, 10, 38, 36, 106, 78, 206, 138, 342, 214, respectively) of 4 match the apo topology.
(6) (a) Chun, H.; Dybtsev, D.; Kim, H.; Kim, K. *Chem. Eur. J.* 2005, 11, 3521-3529. (b) Ma, B.; Mulfort, K.; Hupp, J. *Inorg. Chem.* 2005, 44, 4912-4914.
(7) (a) Chen, B.; Ockwig, N. W.; Millward, A.; Contreras, D.; Yaghi, O. M. *Angew. Chem., Int. Ed.* 2005, 44, 4745-4749. (b) Lin, X.; Jia, J.; Zhao, X.; Thomas, K.; Blake, A.; Walker, G.; Champness, N. R.; Hubberstey, P.; Schroeder, M. *Angew. Chem., Int. Ed.* 2006, 45, 7358-7364.
(8) (a) Eubank, J. F. Ph.D. thesis, University of South Florida, Tampa, Fla., 2008. (b) Horike, S.; Hasegawa, S.; Tanaka, D.; Higuchi, M.; Kitagawa, S. *Chem. Commun.* 2008, 4436-4438. (c) Qin, L.; Hu, J.-S.; Huang, L.-F.; Li, Y.-Z.; Guo, Z.-J.; Zheng, H.-G. *Cryst. Growth Des.* 2010, 10, 4176-4183.
(9) (a) Abourahma, H.; Bodwell, G. J.; Lu, J.; Moulton, B.; Pottie, I. R.; Walsh, R. B.; Zaworotko, M. J. *Cryst. Growth Des.* 2003, 3, 513-519. (b) Perry, J. J.; McManus, G. J.; Zaworotko, M. J. *Chem. Commun.* 2004, 2534-2535.
(10) Chae, H. K.; Kim, J.; Delgado-Friedrichs, O.; O'Keeffe, M.; Yaghi, O. M. *Angew. Chem. Int. Ed.* 2003, 42, 3907-3909. (b) O'Keeffe, M.; Eddaoudi, M.; Li, H.; Reineke, T.; Yaghi, O. M. *J. Solid State Chem.* 2000, 152, 3-20.
(11) Here, we do not consider embed or catenated pairs (i.e. interpenetrating nets) as separate nets.

(12) (a) Delgado-Friedrichs, O.; O'Keeffe, M.; Yaghi, O. M. *Acta Cryst.* 2006, A62, 350-355. (b) Delgado-Friedrichs, O.; O'Keeffe, M. *Acta Cryst.* 2009, A65, 360-363. (c) Nouar, F.; Eubank, J. F.; Bousquet, T.; Wojtas, L.; Zaworotko, M. J.; Eddaoudi, M. *J. Am. Chem. Soc.* 2008, 130, 1833-1835.

(13) Blatova, V. A.; Proserpio, D. M. *Acta Cryst.* 2009, A65, 202-212.

(14) Moulton, B.; Lu, J.; Hajndl, R.; Hariharan, S.; Zaworotko, M. J. *Angew. Chem. Int. Ed.* 2002, 41, 2821-2824.

(15) (a) Breck, D. W. Zeolite Molecular Sieves: Structure, Chemistry, and Use, John Wiley & Sons, Inc.: N.Y., 1974. (b) Park, K. S.; Ni, Z.; Cote, A. P.; Choi, J. Y.; Huang, R.; Uribe-Romo, F. J.; Chae, H. K.; O'Keeffe, M.; Yaghi, O. M. *Proc. Natl. Acad. Sci. USA* 2006, 103, 10186-10191.

Example 3

Brief Introduction:

A new blueprint network for the design and synthesis of porous, functional 3D MOFs has been identified, namely the tbo net. Accordingly, tbo-MOFs based on this unique (3,4)-connected net can be exclusively constructed utilizing a combination of well-known and readily targeted [M(R-BDC)]$_n$ MOF layers, i.e. supermolecular building layers (SBLs), based on the edge transitive 4,4 square lattice (sql), i.e. 2D building units, and a novel pillaring strategy based on four proximal isophthalate ligands from neighboring SBL 4-member rings, i.e. two pair from each layer, covalently cross-linked through an organic quadrangular-core (e.g. tetra-substituted benzene). Our strategy permits rational design and synthesis of isoreticular structures, functionalized and/or expanded, which possess extra-large, nanocapsule-like cages, high porosity, and potential for gas separation and storage, among others. Thus, tbo-MOF serves as an archetype tunable, isoreticular MOF platform for targeting desired applications.

Discussion:

Metal-organic frameworks (MOFs) are a burgeoning class of functional solid-state materials that are already being explored for use in multiple areas from catalysis to surface chemistry, hydrogen storage, and carbon capture'. These promising materials attract scientists, in academia and industry alike, for their unique and readily functionalizable structures. In other words, their design and construction can be directed toward a targeted use, i.e. certain MOFs could be designed as platforms with controlled pore size, shape and functionality for specific applications. To achieve framework design, however, a high degree of predictability must be integrated prior synthesis, and it is still an ongoing challenge to absolutely predict the network topology of the constructed MOF.[2] As such, our group has devoted its efforts to pinpoint particular blueprint frameworks that underpin our design strategies, preferably based on singular, exclusive nets for a combination of specific building blocks,[3] and that are amenable to isoreticular chemistry.[3,4]

Edge transitive nets may be used since they are typically the most appropriate targets in crystal chemistry and are suitable to the practice of reticular chemistry.[5] A given augmented net can be deconstructed into its basic building units equivalent to vertex figures of the parent net (e.g. triangles for 3-connected nodes and squares for 4-connected nodes).[6] The generated (obtained) geometrical information is then employed to determine, design and target prospective molecular building block (MBB) counterparts.[7] That is, such building units, geometric entities, dictate the points of extension of the desired MBBs. The preferred MBBs can then be targeted by a combination of organic ligand synthesis and controlled metal-ligand directed coordination.[8] The latter is the determining and critical factor in the successful practice of isoreticular chemistry, since access to precise reaction conditions is necessary to consistently generate the inorganic MBB in situ.[2]

In our continuous quest to develop new strategies necessary for the rational assembly of MOF platforms, particularly those containing tunable cages (i.e. confined space) and readily amenable to isoreticulation, we reexamined augmented three dimensional edge transitive nets.[3] The deliberate intent is to identify hierarchal building units,[2,9] periodic 0-, 1-, or 2-dimensional building units,[10] which contain elaborate, inbuilt structural information that is preferably distinctive to the given deconstructed parent, augmented net. It should also be mentioned that interconnected cages are of interest due to their great importance for many applications, as has been observed in application-rich zeolites.[10]

We successfully implemented this strategy when we introduced the supermolecular building block (SBB) approach,[2] where sophisticated hierarchical construction information was embedded into the building unit(s), to deliberately assemble, in situ, a metal-organic polyhedron (MOP) with 24 additional, peripheral functional moieties (i.e. 24 points of extension) that, when combined with triangular building units, can exclusively assemble into a singular (3,24)-connected net, rht,[3] having extra-large cages.

Along our quest, we recognized another distinctive net, tbo-a,[3] that exhibits explicit features of a potential blueprint net for logical design and directed assembly of MOF platforms. Uniquely, tbo-a net is composed of 2D periodic arrays of squares, each consistent with an augmented 4,4 square grid or lattice (sql-a),[3] which are cross-linked through 4-connected (quadrangular) pillars (FIG. 4.1*b*), and encompass inherent polyhedral cavities The sql-a net, being one of only two edge transitive 2D nets based on the assembly of squares,[3] is more easily attained in crystal chemistry. In fact, MOFs having sql topology based on square paddlewheel dimer MBBs [M$_2$(O$_2$CR)$_4$(A)$_2$, M=metal, A=axial ligand] bridged by ditopic organic ligands [e.g. terephthalate or isophthalate (BDCs)] are well-known and readily constructed.[8,11] Thus, surface decorated sql-MOFs, e.g. [M(R-BDC)]$_n$, could be employed as supermolecular building layers (SBLs)[11b] amenable to pillaring[12] via cross-linking through a 4-connected organic building block to construct the desired tbo-MOF platform. Ability to consistently generate [M(R-BDC)]$_n$ layers, SBLs formed in situ, while spacing them with organic quadrangle pillars, will permit to preserve the relatively small 4-membered ring (4MR) windows of the SBLs, prohibiting self-interpenetration, while functionalizing and/or enlarging, unilaterally, the intrinsic confined space delimited (e.g. distinct cages) by the quadrangular pillars. This permits access to made-to-order MOFs, and, exploitation of their resultant functionalized nanocages.

To implement our design strategy we designed and synthesized an octa-carboxylate (i.e. tetra-isophthalate) ligand (FIG. 4.2*a*), where an ether linkage was chosen to allow flexibility of the pendant BDC arms, positioned in a square-like geometry, and retain their ability to freely form the intended SBL (sql-MOF). As expected, reactions of the organic quadrangular-core tetra-BDC ligand, 5,5',5'',5'''-[1,2,4,5-phenyltetramethoxy]tetra-isophthalate (L1, FIG. 4.2*a*), with copper have permitted the construction of the desired tbo-a framework, where the sql-MOF SBLs are bridged by the organic quadrangle. Solvothermal reaction between the rectangular-like H$_8$L1 and Cu(NO$_3$)$_2$.2.5H$_2$O in an N,N-dimethylformamide (DMF)/water solution yields a homogeneous crystalline material, purity confirmed by similarities between experimental and calculated X-ray powder diffraction (XRPD) patterns. The as-synthesized compound was characterized by single-crystal X-ray diffraction as [$Cu_4L1$ $(H_2O)_4$·xsolv], (1).

The resulting MOF can be viewed as a pillared sql-MOF based on L1-cores substituting the inter-layer quadrangles, and, essentially, pillaring 2D Cu-(5-R-isophthalate) sql layers (SBLs). Thus, the quadrangular-pillared sql-MOF can be viewed as a 3D MOF, where the L1 core serves as a 4-connected node, the 5-R-isophthalate moiety as a 3-connected node, and the $Cu_2(O_2CR)_4$ paddlewheel cluster as another 4-connected node. Topological analysis of the resultant (3,4)-connected net reveals that the topology of 1 corresponds to the expected tbo,[3] i.e. 1 can be considered as a tbo-MOF (analogous to one prototypical MOF, HKUST-1[13]).

Alternatively, 1 can be interpreted as a MOF comprised of polyhedral cages[2,14] (FIG. 4.2a), specifically face-sharing truncated cuboctahedra[3] [24 functionalized isophthalate ligands connected by 8 copper dimer centers, $Cu_2(O_2CR)_4$, and 4 L1 benzene cores]. Each inorganic paddlewheel MBB is dinuclear and consists of two copper ions with the expected square pyramidal geometry, each coordinated to four oxygen atoms of four carboxylates and one axial water molecule, $CuO_5$. Each carboxylate moiety of the octuply deprotonated L1 ligand coordinates in a bis-monodentate fashion to two copper atoms to form the $Cu_2(O_2CR)_4$ MBBs. The packing of these face-shared (through 4MRs) truncated cuboctahedral cages results in the formation of inter-polyhedra cavities delineating two other cage types, truncated cubes and truncated tetrahedra (FIG. 4.2b).

Thus, the overall neutral framework of 1 consists of three different types of open cages (FIG. 4.2b). The largest, the truncated cuboctahedron having 17.787×18.349 Å diameters (14.387 Å sphere including van der Waals (vdw) radii), is surrounded by 6 truncated cubes and 8 truncated tetrahedra. The truncated cubes have diameters of 15.424 Å (height) and 16.102 Å (width) (12.024 Å vdw sphere), and each is surrounded by six truncated cuboctahedra and eight truncated tetrahedra. The truncated tetrahedra have diameters of 12.521 Å (height) and 10.220 Å (width) (6.820 Å vdw sphere), and are surrounded by four truncated tetrahedra and four truncated cubes.

To confirm the efficacy of our design strategy, we functionalized the quadrangular organic ligand with two extra pendant isophthalate arms (FIG. 4.3a), which, in principle, could also potentially coordinate to metal cations and direct the formation of a different network (albeit, only if the structure deviates from the targeted sql SBLs). To our satisfaction, reactions of 5,5',5'',5''',5'''',5'''''-[1,2,3,4,5,6-phenylhexamethoxy] hexa-isophthalic acid ($H_{12}L2$) with copper under similar reaction conditions as in 1 have permitted the construction of a MOF analogous to 1, where the two added pendant arms are freely pointing into the generated cavities with no metal coordination.

Solvothermal reaction between the rectangular-like $H_{12}L2$ and $Cu(NO_3)_2$·2.5$H_2O$ in a DMF/water solution yields a homogeneous crystalline material, purity confirmed by similarities between experimental and calculated X-ray powder diffraction (XRPD) patterns. The as-synthesized compound was characterized by single-crystal X-ray diffraction as [$Cu_4$ $(H_4L2)(H_2O)_x(DMF)_x$·xsolv], (2). As expected, the desired tbo-MOF is obtained, where the necessary tetra-isophthalate moieties coordinate to Cu, forming paddlewheels, while the two extra isophthalates remain unbound and point into the large polyhedral cavities (FIG. 4.3b).

Additionally, the uniqueness of our pillaring approach to tbo-MOFs should permit the construction of isoreticular MOFs with the same tbo topology via the expansion of the organic linker, specifically extension of the link between the quadrangular benzene core and the isophthalate moieties (FIG. 4.1a), resulting in SBLs pillared and separated at a greater distance by the expanded quadrangle. To support this concept, 5,5',5'',5'''-[1,2,4,5-benzenetetrayltetrakis(4-methyleneoxyphenylazo)]tetra-isophthalic acid ($H_8L3$) was synthesized, where the isophthalate moieties and benzene core of L1 were kept intact, but the length between them was extended by a 4-hydroxyphenyl-1-diazene moiety (FIG. 4.3c). As projected, solvothermal reaction between $H_8L3$ and copper in a DMF/water solution results in green crystals characterized by single-crystal X-ray diffraction studies as [$Cu(L3)(H_2O)_3(DMF)$·xsolv]$_n$, 3, which is a 3D tbo-MOF isoreticular to 1 and 2. The extra-large truncated cuboctahedral cages in 3 are more like nanocapsules (FIG. 4.3d) and possess diameters in the mesoporous range (up to 29.445× 18.864 Å, 26.045×15.464 Å including van der Waals (vdw) radii). The truncated cubes have diameters of 28.682 Å (height) and 15.612 Å (width) (25.282×12.212 Å vdw), and the truncated tetrahedra have diameters of 26.499 Å (height) and 9.081 Å (width) (23.099×5.681 Å vdw).

The total solvent-accessible volumes for 1, 2, and 3 were estimated to be ~72%, ~56%, and ~76%, respectively, by summing voxels more than 1.2 Å away from the framework using PLATON software.[15] Sorption studies, performed on each compound, confirm permanent porosity. Argon sorption isotherms on compounds 1 and 2, are fully reversible type I isotherms, characteristic of microporous materials. The Langmuir apparent surface area for 1 was estimated to be 2896 m$^2$/g, which is higher than the prototypical HKUST-1 (692-1944 m$^2$/g).[13,16] The calculated total free volume was estimated to be 0.97 cm$^3$/g. As anticipated, the effect of ancillary pendant groups in compound 2 is reflected by the reduced surface area and free pore volume, estimated at 1490 m$^2$/g and 0.47 cm$^3$ g$^{-1}$. As a result, isoreticular compounds 1 and 2 are attractive sorbents for the evaluation of the impact of pore size, shape and functionality on sorption energetics and uptake of industrially and environmentally relevant gases such as $CH_4$, $H_2$ and $CO_2$. As a result, isoreticular compounds 1 and 2 are attractive sorbents for the evaluation of the impact of pore size, shape and functionality on sorption energetics and up take of industrially and environmentally relevant gases such as $CH_4$, $H_2$ and $CO_2$.

Accordingly, $H_2$, $CO_2$ and $CH_4$ sorption experiments were carried out at various temperatures and pressures. For $H_2$, the isosteric heat of adsorption ($Q_{st}$) was found to be higher in the case of 2 (vs. 1) over the entire studied range, e.g. 7.6 vs. 6.8 kJ mol$^{-1}$ at low loading; nevertheless, the maximum uptake at 77 K and 1 bar was higher for 1 (2.37 vs. 1.80 wt % for 2). The observed improvement on the $H_2$ sorption energetics in the case of 2 is likely attributed to the combined size and surface effects pertaining to the exposed free carboxylic acids, now reducing the confined space and promoting a localized higher charge density.[17] In the case of $CO_2$, it is anticipated that free carboxylic acids exposed in the pores will enhance the energetics of $CO_2$ sorption; $CO_2$ is recognized to act as a Lewis base leading to relatively strong specific interactions with carboxylic acids.[18] Indeed, the Qst for $CO_2$ was found to be higher in the entire studied range for 2 with a more pronounced difference at low loading, 35.2 kJ mor$^{-1}$ vs. 29.7 kJ mor$^{-1}$ for 1 (FIG. 4.4b). It should be mentioned, that at 258 K the uptake for 2 is more pronounced at reduced pressures vs.

1; this trend is reversed once the uptake reaches 8.5 mmol/mmol (at 1 bar, the max uptake is 10.1 vs. 9.7 mmol/mmol for 1 and 2) (FIG. 4.4a).

In order to further confirm and elucidate the impact of free carboxylic acids on the $CO_2$ sorption energetics in the case of compound 2, we elected to perform comparative sorption studies, at room temperature and elevated pressures, with a quadrupole-less sorbate probe molecule, namely $CH_4$. In fact, a more pronounced difference between $CO_2$ and $CH_4$ uptake, for 2 vs. 1, is observed in the lower pressure range (i.e. 0-5 bar) of the sorption isotherms (FIG. 4.4c), indicative of enhanced $CO_2$ interactions with the framework also evidenced by the steepness of the $CO_2$ sorption isotherm at low loading for 2. This result is in complete agreement with the relatively high $Q_{st}$ observed at low loading for compound 2 vs. 1. It is worth mentioning, the $CO_2$ sorption isotherms at 298K for 1 and 2 intersect around 6 bar and at comparable uptake (~8.5 mmol/mmol) to that observed in the sorption isotherms at lower temperature (258K) (FIG. 4.4a). Also, a noticeable difference for $CH_4$ sorption isotherms is primarily only observed at higher studied pressures, which is likely correlated to the difference in pore size distribution between compounds 1 and 2., i.e. $CH_4$ specific interactions with the free carboxylic acid groups are relatively less dominant than $CO_2$. It is apparent that functionalizing pores with moieties that can favorably interact with $CO_2$ will permit to achieve a made-to-order MOF with desired affinity and capacity for $CO_2$ capture and storage.

We have successfully adapted a modular pillaring strategy to the design and synthesis of isoreticular tbo-MOF platforms, including functionalization and expansion of cavities. The novel tbo-MOFs (i.e. quadrangular pillared sql-MOFs) maintain thermal stability up to nearly 300° C. and exhibit permanent porosities higher than observed for the analogous HKUST-1 material. The addition of pendant functional groups, in this case carboxylic acids, enhances affinity for guest molecules, particularly $CO_2$. Further sorption studies are underway to evaluate other potential guest molecules. Future work will include encapsulation of porphyrins and analogous molecules, as well as their corresponding catalytic studies. Also, the facile nature of MOF synthesis combined with our platform technique will allow us to integrate a variety of metals (e.g. Mo-, Fe-, and Cr-HKUST-1 analogues are already known[19], and numerous metals are known to form the paddlewheel MBB[11a]). In addition, this approach, based on the pillaring of supermolecular building layers (SBLs) as the main periodic building units, will permit the generation of MOFs with larger surface areas that can be readily functionalized prior the assembly process. Work is in progress to introduce various additional functionalities for targeted applications (e.g. various amines to evaluate their impact on $CO_2$ uptake), such as gas separation applications and development of thin film-based MOFs.

REFERENCES, each of which is incorporated herein by reference (1) *Metal-Organic Frameworks: Design and Application*; L. MacGillivray, Ed.; WILEY-VCH Verlag GmbH & Co. KGaA: Weinheim, 2010 and references therein.
(2) Nouar, F.; Eubank, J. F.; Bousquet, T.; Wojtas, L.; Zaworotko, M. J.; Eddaoudi, M. *J. Am. Chem. Soc.* 2008, 130, 1833-1835.
(3) O'Keeffe, M.; Peskov, M. A.; Ramsden, S. J.; Yaghi, O. M. *Accts. Chem. Res.* 2008, 41, 1782-1789 (RCSR).
(4) Yaghi, O. M.; O'Keeffe, M.; Ockwig, N. W.; Chae, H. K.; Eddaoudi, M.; Kim, J. *Nature* 2003, 423, 705-714.
(5) (a) Delgado-Friedrichs, O.; O'Keeffe, M.; Yaghi, O. M. *Acta Cryst.* 2006, A62, 350-355. (b) Delgado-Friedrichs, O.; O'Keeffe, M. *Acta Cryst.* 2009, A65, 360-363.
(6) Ockwig, N. W.; Delgado-Friedrichs, O.; O'Keeffe, M.; Yaghi, O. M. *Acc. Chem. Res.* 2005, 38, 176-182.
(7) (a) Stein, A.; Keller, S. W.; Mallouk, T. E. *Science* 1993, 259, 1558-1564. (b) Ferey, G. *J. Solid State Chem.* 2000, 152, 37-48. (c) Eddaoudi, M.; Kim, J.; Rosi, N.; Vodak, D.; Wachter, J.; O'Keeffe, M.; Yaghi, O. M. *Science* 2002, 295, 469-472. (d) Kitagawa, S.; Kituara, R.; Noro, S.-I. *Angew. Chem., Int. Ed.* 2004, 43, 2334-2375.
(8) Tranchemontagne, D. J.; Mendoza-Cortes, J. L.; O'Keeffe, M.; Yaghi, O. M. *Chem. Soc. Rev.* 2009, 38, 1257-1283.
(9) Sudik, A. C.; Cote, A. P.; Wong-Foy, A. G.; O'Keeffe, M.; Yaghi, O. M. *Angew. Chem., Int. Ed.* 2006, 45, 2528-2533.
(10) Baerlocher, Ch.; McCusker, L. B. Database of Zeolite Structures: http://www.iza-structure.org/databases/.
(11) (a) Allen, F. H. *Acta Cryst.* 2002, B58, 380-388 (CSD). (b) Eubank, J. F.; Wojtas, L.; Hight, M. R.; Bousquet, T.; Kravtsov, V. Ch.; Eddaoudi, M. *J. Am. Chem. Soc.* 2011, *ASAP* (DOI: 10.1021/ja203898s).
(12) 3 basic types of pillaring: a) Axial-to-axial pillaring: Ma, B.; Mulfort, K.; Hupp, J. *Inorg. Chem.* 2005, 44, 4912-4914. b) Ligand-to-ligand pillaring: Chen, B.; Ockwig, N. W.; Millward, A.; Contreras, D.; Yaghi, O. M. *Angew. Chem., Int. Ed.* 2005, 44, 4745-4749. c) Axial-to-ligand pillaring: see reference 11 b.
(13) Chui, S. S. Y.; Lo, S. M. F.; Charmant, J. P. H.; Orpen, A. G.; Williams, I. D. *Science* 1999, 283, 1148-1150.
(14) (a) Liu, Y.; Kravtsov, V. Ch.; Eddaoudi, M. *Angew. Chem. Int. Ed.* 2008, 47, 8446-8449. (b) Sava, D. F.; Kravtsov, V. Ch.; Nouar, F.; Wojtas, L.; Eubank, J. F; Eddaoudi, M. *J. Am. Chem. Soc.* 2008, 130, 3768-3770. (c) Liu, Y.; Kravtsov, V. Ch.; Larsen, R.; Eddaoudi, M. *Chem. Commun.* 2006, 148, 1488-1490. (d) Férey, G.; Mellot-Draznieks, C.; Serre, C.; Millange, F.; Dutour, J.; Surblë, S.; Margiolaki, I. *Science* 2005, 309, 2040-2042.
(15) PLATON: (a) Spek, T. L. *Acta Cryst.* 1990, A46, 194-201. (b) Spek, T. L. *Acta Cryst.* 1990, A46, c34.
(16) Wong-Foy, A. G.; Matzger, A. J.; Yaghi, O. M. *J. Am. Chem. Soc.* 2006, 128, 3494-3495.
(17) Liu, Y.; Eubank, J. F.; Cairns, A. J.; Eckert, J.; Kravtsov, V. Ch.; Luebke, R.; Eddaoudi, M. *Angew. Chem. Int. Ed.* 2007, 46, 3278-3283.
(18) (a) Bell, P. W.; Thote, A. J.; Park, Y.; Gupta, R. B.; Roberts, C. B. *Ind. Eng. Chem. Res.* 2003, 42, 6280-6289. (b) Torrisi, A.; Mellot-Draznieks, C.; Bell, R. G. *J. Chem. Phys.* 2010, 132, 044705.
(19) $Mo_3(BTC)_2$: Kramer, M.; Schwarz, U.; Kaskel, S. *J. Mater. Chem.* 2006, 16, 2245-2248. $Fe_3(BTC)_2$: Xie, L.; Liu, S.; Gao, C.; Cao, R.; Cao, J.; Sun, C.; Su, Z. *Inorg. Chem.* 2007, 46, 7782-7788. $Cr_3(BTC)_2$: Murray, L. J.; Dinca, M.; Yano, J.; Chavan, S.; Bordiga, S.; Brown, C. M.; Long, J. R. *J. Am. Chem. Soc.* 2010, 132, 7856-7857.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the units of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:
1. A chemical assembly, comprising:
a multidimensional metal-organic framework (MOF) having a plurality of supermolecular building layers (SBLs), where the SBL comprises:
an inorganic molecular building block (MBB);
a trigonal-pillar, where the trigonal pillar comprises a bridging ligand moiety and a pillar moiety,
where the bridging ligand moiety is:

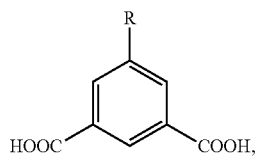

where R can be an alkoxy linker attached to the pillar moiety or the pillar moiety, and
where the pillar moiety is a pyridine.

2. The chemical assembly of claim 1, wherein the MOF includes ligand-to-axial (L-A) pillaring.

3. The chemical assembly of claim 1, wherein the trigonal-pillar is selected from the group consisting of:

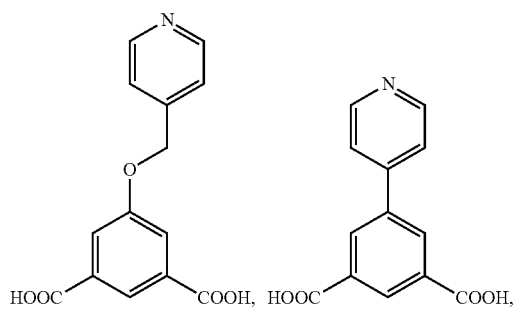

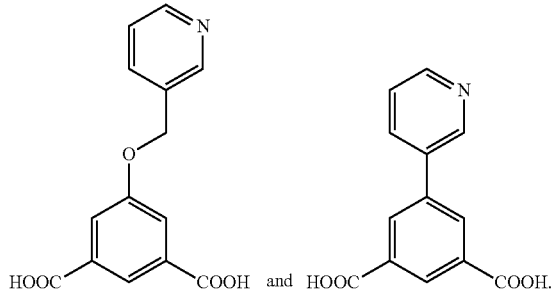

4. The chemical assembly of claim 1, wherein the MOF is configured as a (3,6)-connected net.

5. The chemical assembly of claim 4, wherein the (3,6)-connected net is in an anh, ant, apo, brk, pyr or rtl configuration.

6. The chemical assembly of claim 1, wherein the inorganic MBB includes a metal or cluster of metals and coordinating functional groups of the trigonal-pillar.

7. The chemical assembly of claim 6, wherein the metal is $M^{1+}$, $M^{2+}$, $M^{3+}$, $M^{4+}$, or a metal with an oxidation state of +5, +6, +7, or +8, wherein the metal coordinates with one or more of the bridging ligands.

8. The chemical assembly of claim 1, wherein the inorganic MBB is selected from a 4-connected node (4-connected nodes), a 3-connected node (3-connected nodes), a 5-connected node (5-connected nodes), or a 6-connected node (6-connected nodes).

9. The chemical assembly of claim 1, wherein the topology of the SBL is selected from the group consisting of sql, kgm, hcb, bru, hxl, and kgd.

10. The chemical assembly of claim 1, wherein the MOF is selected from a porous MOF or a nonporous MOF that can be deconstructed into one or SBLs.

11. The chemical assembly of claim 1, wherein the MOF includes of a polyhedral cage.

12. A chemical assembly, comprising:
a supermolecular building layer (SBL), where the SBL comprises:
an inorganic molecular building block (MBB);
a trigonal-pillar, where the trigonal pillar comprises a bridging ligand moiety and a pillar moiety,
where the bridging ligand moiety is:

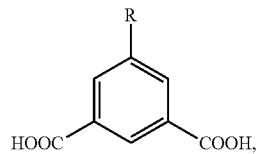

where R can be an alkoxy linker attached to the pillar moiety or the pillar moiety, and
where the pillar moiety is a pyridine.

13. The chemical assembly of claim 12, wherein the trigonal-pillar is selected from the group consisting of: 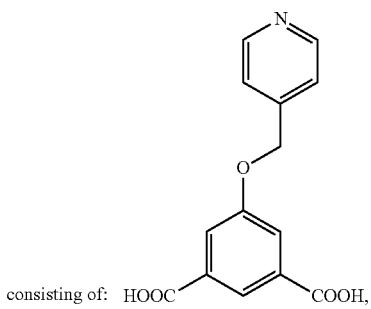

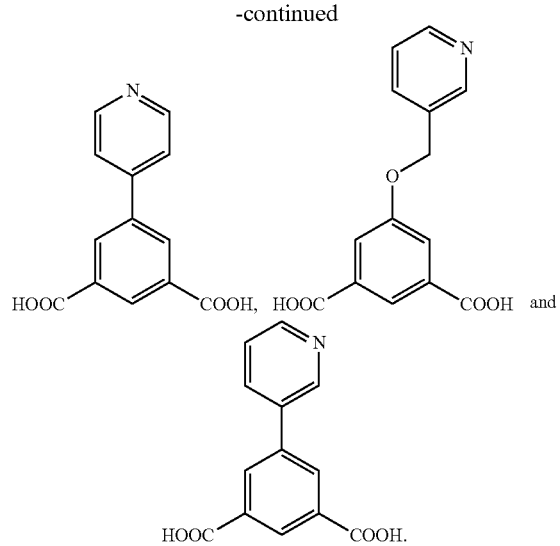
14. The chemical assembly of claim 12, wherein the inorganic MBB includes a metal or cluster of metals and coordinating functional groups of the trigonal-pillar.
* * * * *